(12) United States Patent
Gu et al.

(10) Patent No.: US 11,980,598 B2
(45) Date of Patent: May 14, 2024

(54) N-(2-(SUBSTITUTED-NAPHTH-1-YL)ETHYL) SUBSTITUTED AMIDE COMPOUND, PREPARATION AND USES THEREOF

(71) Applicant: BEIJING GREATWAY PHARMACEUTICAL TECHNOLOGY CO., LTD., Beijing (CN)

(72) Inventors: Wei Gu, Beijing (CN); Hong Tao, Beijing (CN)

(73) Assignee: Beijing Greatway Pharmaceutical Technology Co., Ltd., Beijing (CN)

( * ) Notice: Subject to any disclaimer, the term of this patent is extended or adjusted under 35 U.S.C. 154(b) by 170 days.

(21) Appl. No.: 16/629,908

(22) PCT Filed: Jul. 11, 2018

(86) PCT No.: PCT/CN2018/095325
§ 371 (c)(1),
(2) Date: Jan. 9, 2020

(87) PCT Pub. No.: WO2019/011279
PCT Pub. Date: Jan. 17, 2019

(65) Prior Publication Data
US 2021/0077431 A1  Mar. 18, 2021

(30) Foreign Application Priority Data
Jul. 12, 2017  (CN) .......................... 201710567041.2

(51) Int. Cl.
| | | |
|---|---|---|
| C07C 233/18 | (2006.01) | |
| A61K 9/20 | (2006.01) | |
| A61K 31/165 | (2006.01) | |
| A61K 45/06 | (2006.01) | |
| A61P 25/22 | (2006.01) | |
| A61P 25/24 | (2006.01) | |
| C07C 231/14 | (2006.01) | |

(52) U.S. Cl.
CPC .......... *A61K 31/165* (2013.01); *A61K 9/2009* (2013.01); *A61K 9/2013* (2013.01); *A61K 9/2018* (2013.01); *A61K 9/2027* (2013.01); *A61K 9/2059* (2013.01); *A61K 45/06* (2013.01); *A61P 25/22* (2018.01); *A61P 25/24* (2018.01); *C07C 231/14* (2013.01); *C07C 233/18* (2013.01); *C07B 2200/05* (2013.01)

(58) Field of Classification Search
CPC .. A61K 31/165; A61K 9/2009; A61K 9/2013; A61K 9/2018; A61K 9/2027; A61K 9/2059; A61K 45/06; A61P 25/22; A61P 25/24; A61P 1/00; A61P 3/00; A61P 9/00; A61P 25/00; A61P 25/18; A61P 25/20; C07C 231/14; C07C 233/18; C07C 231/00; C07C 231/12; C07B 2200/05; C07B 59/001
See application file for complete search history.

(56) References Cited

U.S. PATENT DOCUMENTS

2008/0280991 A1  11/2008  Gant et al.

FOREIGN PATENT DOCUMENTS

| | | | |
|---|---|---|---|
| CN | 102206170 A | 10/2011 | |
| CN | 104130154 A | 11/2014 | |
| CN | 104230742 A | 12/2014 | |
| CN | 104292125 A | 1/2015 | |
| JP | 11502336 A | 2/1999 | |
| JP | 11263761 A | 9/1999 | |
| JP | 11510804 A | 9/1999 | |
| WO | WO-9529173 A1 | 11/1995 | |
| WO | WO-2008137461 A1 * | 11/2008 | .............. A61P 25/00 |
| WO | WO-2008141033 A1 | 11/2008 | |
| WO | WO-2012046253 A2 | 4/2012 | |
| WO | WO-2012093402 A1 * | 7/2012 | ........... C07C 231/12 |

OTHER PUBLICATIONS

Williams et al. (Foye's Principles of Medicinal Chemistry, 5th Edition, pp. 50 and 59-61, 2002) (Year: 2002).*
Lu et al (Expert Opin. Drug Discov. (2012) 7(5):375-383, cited in a previous Office Action) (Year: 2012).*
Yous, S et al.,Novel Naphthalenic Ligands with High Affinity for the Melatonin Receptor,Journal of Medicinal Chemistry,Apr. 1, 1992.
Translation of International Search Report for International Application No. PCT/CN2018/095325, dated Sep. 18, 2018.
First Office Action issued by the Japanese Patent Application 2020-523478, dated Feb. 8, 2021, with an English translation.
NPL—Frohn, M. A., et al. "Structure-activity relationship of melatonin an alogs", Life Sciences, 1980,27(22),2043-2046.

(Continued)

*Primary Examiner* — Rayna Rodriguez
(74) *Attorney, Agent, or Firm* — Wolf, Greenfield & Sacks, P.C.

(57) ABSTRACT

The present disclosure relates to an N-(substituted naphthylethyl) substituted amide compound and uses thereof serving as a melatonin receptor agonist and 5-HT$_{2C}$ receptor antagonist, and specifically relates to the compound of formula (I) or a pharmaceutically acceptable salt thereof, a solvate or a mixture of them, and a pharmaceutical composition, where X, R$_1$, and R$_2$ are as defined in the present text.

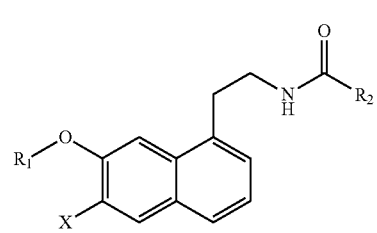

16 Claims, 2 Drawing Sheets

(56) References Cited

OTHER PUBLICATIONS

Ettaoussi et al., "Design, synthesis and pharmacological evaluation of new series of naphthalenic analogues as melatoninergic (MT1/MT2) and serotoninergic 5-HT2C dual ligands (I)", European Journal of Medicinal Chemistry, 49, pp. 310-323 (2012).

Blass, Basic principles of drug discovery and development. Elsevier; Apr. 24, 2015, p. 340.

* cited by examiner

N-(2-(SUBSTITUTED-NAPHTH-1-YL)ETHYL) SUBSTITUTED AMIDE COMPOUND, PREPARATION AND USES THEREOF

The present application claims priority to Chinese patent application No. 201710567041.2 filed on Jul. 12, 2017, the entire disclosure of which is incorporated herein by reference.

TECHNICAL FIELD

The present disclosure relates to an N-(2-(substituted-naphthalen-1-yl)ethyl)-substituted amide compound, a process for preparing the same, a pharmaceutical composition, and a method and use for preventing/treating a disease or condition such as melatoninergic system disease, stress, anxiety, seasonal affective disorder, cardiovascular disease, digestive system disease, schizophrenia, phobia, depression, major depression, sleep disorder, dyssomnia, insomnia or fatigue due to jet-lag, or body weight deregulation.

BACKGROUND

A melatonin receptor (MT) agonist is a new class of compounds with antidepressant, anti-anxiety, circadian cycle and body weight regulation effects. Compared with the currently commonly used selective serotonin (5-HT) reuptake inhibitor (SSRI) and serotonin-norepinephrine reuptake inhibitor (SNRI) type of antidepressants, a melatonin receptor agonist type of compounds have several advantages in application, mainly less adverse reactions, including weight gain, adverse effects on sexual function, withdrawal reactions, and the like. This class of drugs has attracted much attention due to its new mechanism and good clinical performance. Among them, four drugs are currently available on the market, namely, Melatonin, Agomelatine, Ramelteon, and Tasimelteon; and there is also TIK301 in clinical phase II study.

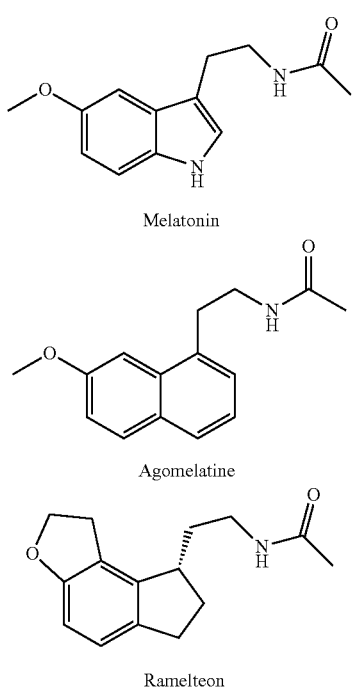

Melatonin

Agomelatine

Ramelteon

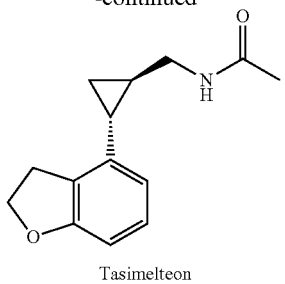

Tasimelteon

Agomelatine, developed by Servier, France, is the only melatonin receptor agonist type of antidepressant approved for clinical use. Agomelatine is special compared to other melatonin receptor agonists. It is not only an agonist of melatonin receptor $MT_1$ and $MT_2$ (inhibition constant Kis $6.15\times10^{-11}$ mol/L and $2.68\times10^{-10}$ mol/L, respectively), but also an antagonist of $5\text{-}HT_{2C}$ receptor ($IC_{50}=2.7\times10^{-7}$ mol/L). Clinical studies have shown that it has a significant anti-depressant effect, a faster onset of action, and a good effect on depression and accompanying anxiety disorders; compared with SSRIs such as paroxetine, it has a faster onset of action and may have a better effect on major depressive disorder (MDD) since it can increase the continuity and quality of sleep in MDD patients; at the same time, its negative impact on sexual function is significantly less than other antidepressants.

The drug was launched in Europe in 2009 and was approved for import in China in April 2011. At present, its clinical indication is adult depression, and clinical research on anxiety and sleep disorders is also underway.

As a multi-targeted antidepressant with a completely new mechanism, Agomelatine is targeted as a "blockbuster" class of new drug before it comes into the market, but the response after it appears on the market is not as expected. The main reasons include its unsatisfactory metabolic property in vivo and its adverse effects on liver enzymes.

The oral absorption of Agomelatine is rapid and sufficient (over 80%), but due to the first-pass effect of the liver, it is metabolized by CYP1A2 (about 90%) and CYP2C9 (about 10%) with demethylation and hydroxylation, eventually producing a dihydroxy metabolite that has no affinity to the $5\text{-}HT_{2C}$ receptor and has a low affinity to the MT receptor (approximately 3-4 orders of magnitude lower), thereby losing its effect.

The absolute bioavailability of Agomelatine is below 5%, and some literatures even indicate that this value is only 1% in an actual measurement (e.g., Australian Public Assessment Report for Agomelatine, Submission No: PM-2009-00483-3-1).

Due to the poor oral bioavailability of the drug, it is necessary to increase the dosage in clinical applications. Poor oral bioavailability can also result in significant individual differences. Agomelatine has an adverse effect on liver enzymes, and more than 1% of patients will have an increase in ALT/AST (three times above the normal upper limit). This adverse reaction is idiosyncratic and also dose-related. Therefore, it is particularly important to reduce the oral dose and reduce liver damage by increasing the oral bioavailability of such compounds.

Therefore, there is still a need to develop a new type of drugs.

SUMMARY OF THE INVENTION

The inventors have obtained a compound represented by Formula I through intensive research and creative labor. The inventors have surprisingly found that a compound of formula I, or a pharmaceutically acceptable salt or solvate thereof, or a mixture thereof, has the following excellent pharmaceutical properties: exhibiting comparable or higher receptor affinity in a receptor binding test ($MT_1$, $MT_2$ and $5-HT_{2C}$) compared to Agomelatine; exhibiting greater metabolic stability in pharmacokinetic tests in vitro and in vivo; and exhibiting greater pharmacodynamic activity in whole animal tests and at the same time better safety in acute toxicity tests.

The results of the study indicate that the compound of formula I, or a pharmaceutically acceptable salt or solvate thereof, or a mixture thereof, can be used for preventing/treating a disease or condition such as melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag, or body weight deregulation.

A first aspect disclosed herein relates to the following:

1. A compound of formula I, or a pharmaceutically acceptable salt or solvate thereof, or a mixture thereof,

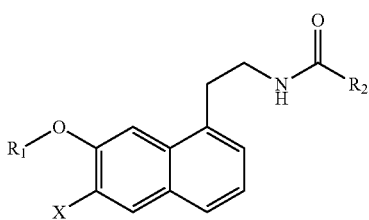

wherein:
X is H or halogen;
$R_1$ is $CH_3$ or $CD_3$;
$R_2$ is $CH_3$, $CD_3$ or $C_2H_5$;
with the proviso that when X is H, $R_2$ is $C_2H_5$.

2. The compound of Embodiment 1, wherein $R_2$ is $CH_3$ or $C_2H_5$.

3. The compound of Embodiment 1 or 2, wherein X is fluorine or chlorine.

4. The compound of any one of Embodiments 1 to 3, wherein $R_1$ is $CD_3$.

5. The compound of any one of Embodiments 1 to 4, wherein X is fluorine or chlorine, and $R_1$ is $CD_3$.

6. The compound of any one of Embodiments 1 to 5, which is selected from the group consisting of:
N-(2-(6-chloro-7-deuteromethoxy-naphthalen-1-yl)ethyl) acetamide;
N-(2-(6-chloro-7-methoxy-naphthalen-1-yl)ethyl)acetamide;
N-(2-(6-fluoro-7-deuteromethoxy-naphthalen-1-yl)ethyl) acetamide;
N-(2-(6-fluoro-7-methoxy-naphthalen-1-yl)ethyl)acetamide;
N-(2-(6-chloro-7-deuteromethoxy-naphthalen-1-yl)ethyl) propanamide;
N-(2-(6-chloro-7-methoxy-naphthalen-1-yl)ethyl)propanamide;
N-(2-(6-fluoro-7-methoxy-naphthalen-1-yl)ethyl)propanamide;
N-(2-(6-chloro-7-deuteromethoxy-naphthalen-1-yl)ethyl) acetamide hydrochloride hydrate;
N-(2-(6-chloro-7-deuteromethoxy-naphthalen-1-yl)ethyl) acetamide hydrochloride;
N-(2-(6-chloro-7-methoxy-naphthalen-1-yl)ethyl)acetamide hydrochloride hydrate;
N-(2-(6-chloro-7-methoxy-naphthalen-1-yl)ethyl)acetamide hydrochloride;
N-(2-(6-chloro-7-methoxy-naphthalen-1-yl)ethyl)acetamide hydrobromate hydrate;
N-(2-(6-chloro-7-methoxy-naphthalen-1-yl)ethyl)acetamide sulfate;
N-(2-(6-chloro-7-methoxy-naphthalen-1-yl)ethyl)acetamide methanesulfonate; and
N-(2-(6-fluoro-7-methoxy-naphthalen-1-yl)ethyl)acetamide hydrochloride hydrate.

7. A pharmaceutical composition, comprising:
a therapeutically and/or prophylactically effective amount of the compound of formula I, or the pharmaceutically acceptable salt or solvate thereof, or the mixture thereof according to any one of Embodiments 1-6, and
a pharmaceutically acceptable adjuvant.

8. A pharmaceutical combination, comprising:
a) one or more first active ingredient(s) selected from the compound of formula I, or the pharmaceutically acceptable salt or solvate thereof, or the mixture thereof according to any one of Embodiments 1-6, and
b) one or more additional active ingredient(s) selected from the group consisting of a melatonin receptor agonist and a $5-HT_{2C}$ receptor antagonist.

9. Use of the compound of formula I, or the pharmaceutically acceptable salt or solvate thereof, or the mixture thereof according to any one of Embodiments 1-6, in the manufacture of a melatonin receptor agonist.

10. Use of the compound of formula I, or the pharmaceutically acceptable salt or solvate thereof, or the mixture thereof according to any one of Embodiments 1-6, in the manufacture of a $5-HT_{2C}$ receptor antagonist.

11. Use of the compound of formula I, or the pharmaceutically acceptable salt or solvate thereof, or the mixture thereof according to any one of Embodiments 1-6, in the manufacture of a medicament for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation.

12. A method for synthesizing the compound of formula I of Embodiment 1, comprising:
carrying out a Friedel-Crafts reaction between methoxybenzene or methoxybenzene ortho-substituted with halogen and succinic anhydride in the presence of a catalyst to give an aromatic ketone, i.e., intermediate 1;
reducing a carbonyl group of ketone in the intermediate 1 to a methylene group with triethylsilane to give an intermediate 2;
cyclizing the intermediate 2 under the action of an acidic catalyst to give tetralin, i.e., intermediate 3;
cyanating the intermediate 3 with cyanoacetic acid to give dihydronaphthylacetonitrile, i.e., intermediate 4;
dehydrogenating the intermediate 4 to give naphthylacetonitrile, i.e., intermediate 5; and
reacting the intermediate 5 with sodium borohydride and acetic anhydride or propionic anhydride in the presence of a catalyst nickel chloride hexahydrate to give an acetamide or propionamide compound.

13. The method of Embodiment 12, further comprising:
dissolving the acetamide or propionamide compound in toluene to react with anhydrous aluminum trichloride to give a naphthol; and
reacting the naphthol with deuterated methyl iodide to give a deuterated acetamide or propionamide compound.

14. The method of Embodiment 12 or 13, further comprising:
reacting the acetamide or propionamide compound or the deuterated acetamide or propionamide compound with an acid to form a salt.

15. The compound of formula I, or the pharmaceutically acceptable salt or solvate thereof, or the mixture thereof according to any one of Embodiments 1-6, for use as a medicament.

16. The compound of formula I, or the pharmaceutically acceptable salt or solvate thereof, or the mixture thereof according to any one of Embodiments 1-6, for use in preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation.

17. A method for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, the method comprising administering to a subject in need thereof the compound of formula I, or the pharmaceutically acceptable salt or solvate thereof, or the mixture thereof according to any one of Embodiments 1-6.

18. A method for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, the method comprising administering the pharmaceutical composition of Embodiment 7 to a subject in need thereof.

19. A method for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, the method comprising administering the pharmaceutical combination of Embodiment 8 simultaneously or sequentially to a subject in need thereof.

20. A pharmaceutical composition for preventing or treating a disease or condition selected from the group consisting of melatoninergic system disease, cardiovascular disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, comprising the compound of formula I, or the pharmaceutically acceptable salt or solvate thereof, or the mixture thereof according to any one of Embodiments 1-6.

A second aspect disclosed herein relates to use of a compound, or a pharmaceutically acceptable salt or solvate thereof, or a mixture thereof in any one of the above embodiments, for preventing or treating a disease or condition.

A third aspect disclosed herein relates to use of a compound, or a pharmaceutically acceptable salt or solvate thereof, or a mixture thereof in any one of the above embodiments, for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, in a subject in need thereof.

A fourth aspect disclosed herein relates to a method for preparing a compound, or a pharmaceutically acceptable salt or solvate thereof, or a mixture thereof in any one of the above embodiments.

EMBODIMENTS

Definitions

Figure 1:
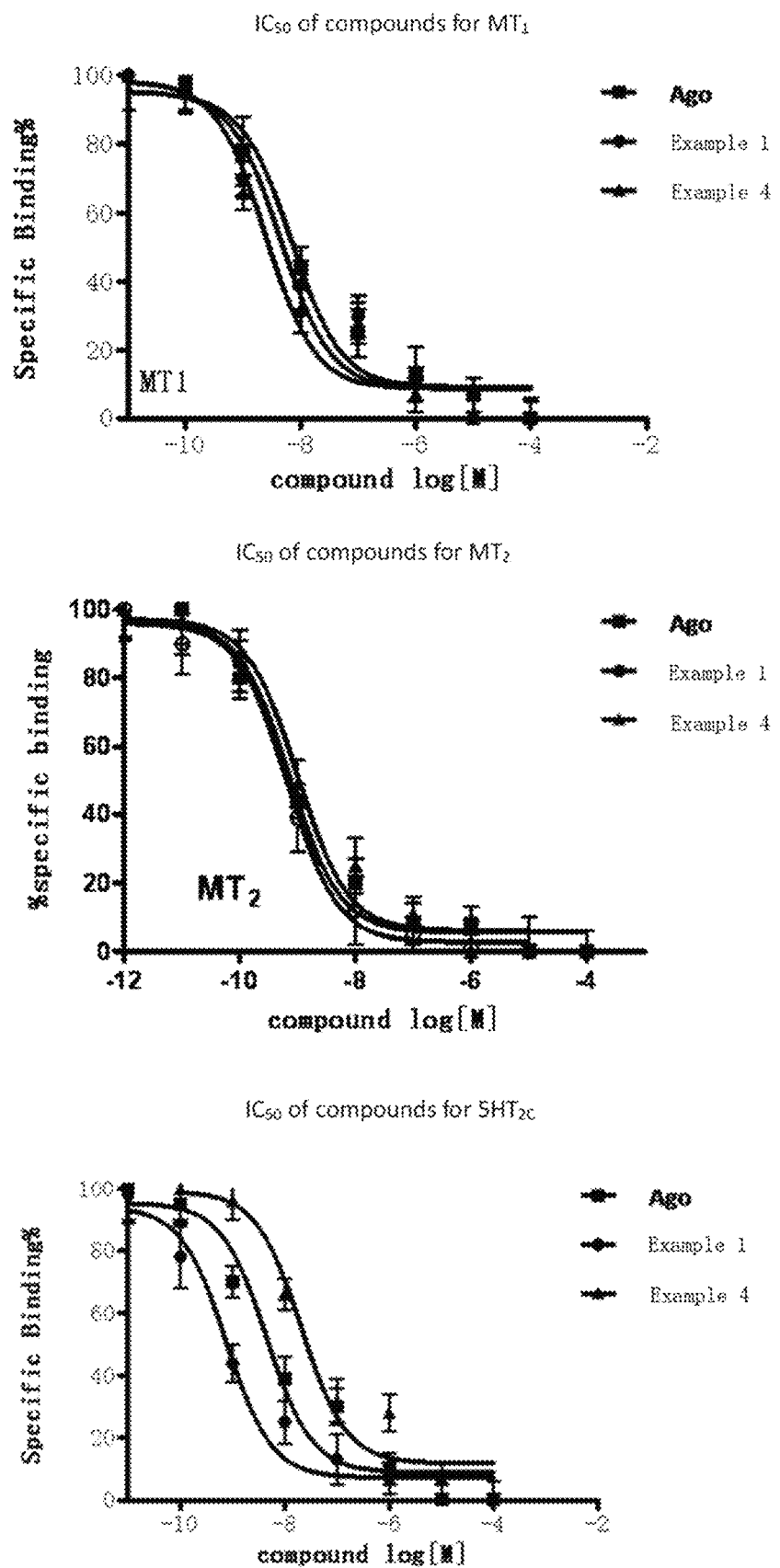
FIG. 1 shows the results of the $MT_1$, $MT_2$ and $5HT_{2C}$ receptor binding tests for the compounds of Examples 1 and 4 and the control Ago.

The term "metabolic stability" as used herein refers to the ability of a compound to enter and stably exist in a body in the form of a prototype drug, without being metabolized to other structural forms.

The term "pharmaceutically acceptable" as used herein means that a compound or composition is chemically and/or toxicologically compatible with other ingredients that make up the formulation and/or with a human or mammal in which a disease or condition is prevented or treated with the compound or composition.

The term "subject" or "patient" as used herein includes a human and a mammal.

The term "adjuvant" as used herein refers to an excipient or vehicle for administering a compound, including, but not limited to, diluent, disintegrant, precipitation inhibitor, surfactant, glidant, binder, lubricant, and coating materials, etc. An adjuvant is generally described in "Remington's Pharmaceutical Sciences" by E. W. Martin. Examples of adjuvants include, but are not limited to, aluminum monostearate, aluminum stearate, carboxymethylcellulose, sodium carboxymethylcellulose, crospovidone, glyceryl isostearate, glyceryl monostearate, hydroxyethyl cellulose, hydroxymethyl cellulose, hydroxyoctacosyl hydroxystearate, hydroxypropyl cellulose, hydroxypropyl methyl cellulose, lactose, lactose monohydrate, magnesium stearate, mannitol, microcrystalline cellulose, and the like.

In the context of the present application, the term "treatment," "treat," or "treating" may also include prophylaxis unless specifically stated to the contrary.

The term "solvate" as used herein refers to a complex formed by combining a compound of formula I or a pharmaceutically acceptable salt thereof and a solvent. It is understood that although any solvate of a compound of formula I used in the treatment of a disease or condition as described herein may provide various properties including pharmacokinetic properties, it would result in the compound of formula I once being absorbed into the subject, and the use of a compound of formula I encompasses use of any solvate of the compound of formula I respectively.

The term "hydrate" refers to the case where the solvent in the above term "solvate" is water.

It is to be further understood that a compound of formula I or a pharmaceutically acceptable salt thereof can be isolated as a solvate, and thus any such solvate is included within the scope disclosed herein. For example, a compound of formula I or a pharmaceutically acceptable salt thereof may be present in an unsolvated form or a solvated form with a pharmaceutically acceptable solvent such as water, ethanol, and the like.

The term "pharmaceutically acceptable salt" refers to a relatively non-toxic, inorganic or organic acid addition salt of a compound disclosed herein. See, for example, S. M. Berge et. al, "Pharmaceutical Salts," J. Pharm. Sci. 1977, 66, 1-19. For example, an inorganic acid is hydrochloric, hydrobromic, hydroiodic, sulfuric, phosphoric, or nitric acid; and an organic acid is formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, or sulfosalicylic acid, and the like. For example, a pharmaceutically acceptable salt can be formed by using HCl (or a solution of hydrochloric acid), HBr (or a solution of hydrobromic acid), methanesulfonic acid, sulfuric acid, tartaric acid or fumaric acid and a compound of formula I.

It is to be understood that the term "compound disclosed herein" as used in the present application may include, according to the context, an amide compound of formula I, a pharmaceutically acceptable salt thereof, a solvate thereof, a solvate of a pharmaceutically acceptable salt thereof, and a mixture of them.

At least one embodiment disclosed herein provides a compound of formula I, or a pharmaceutically acceptable salt or solvate thereof, or a mixture thereof,

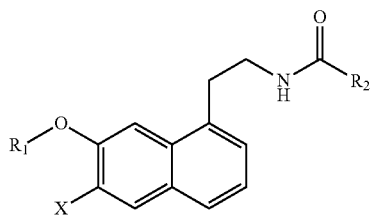

I wherein:
X is H or halogen;
$R_1$ is $CH_3$ or $CD_3$;
$R_2$ is $CH_3$ or $C_2H_5$;
with the proviso that when X is H, $R_2$ is not $CH_3$.

Agomelatine (X is H; both $R_1$ and $R_2$ are $CH_3$) and d3-Agomelatine (X is H; $R_1$ is $CD_3$; $R_2$ is $CH_3$) are excluded from the structure of formula I,

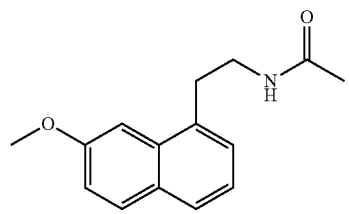

Agomelatine

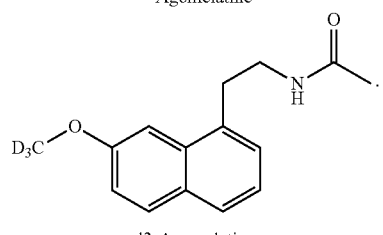

d3-Agomelatine

In one embodiment, X is F, Cl, Br or I; for example, F or Cl.

In one embodiment, $R_1$ is $CH_3$.
In one embodiment, $R_1$ is $CD_3$.
In one embodiment, X is F, Cl, Br or I, and $R_1$ is $CD_3$.
In one embodiment, X is F, Cl or Br, and $R_1$ is $CD_3$.
In one embodiment, X is F or Cl, and $R_1$ is $CD_3$.
In one embodiment, X is Cl, and $R_1$ is $CD_3$.
In one embodiment, X is Cl, and $R_1$ is $CD_3$, and $R_2$ is $CH_3$.

A pharmaceutical complex provided in at least one embodiment disclosed herein may comprise a complex form of a compound of formula I with HCl, HBr, methanesulfonic acid, sulfuric acid, tartaric acid, or fumaric acid, and may also comprise a corresponding solvate (e.g., hydrate) form thereof.

In an exemplary embodiment, the compound is selected from compounds or salt/hydrate thereof in Table 1 below:

TABLE 1

Example compounds

| Number | Compound name | Structural formula |
|---|---|---|
| 1 | N-(2-(6-chloro-7-deuteromethoxy-naphthalen-1-yl)ethyl)acetamide | |

TABLE 1-continued

Example compounds

| Number | Compound name | Structural formula |
|---|---|---|
| 2 | N-(2-(6-chloro-7-methoxy-naphthalen-1-yl)ethyl)acetamide | |
| 3 | N-(2-(6-fluoro-7-deuteromethoxy-naphthalen-1-yl)ethyl)acetamide | |
| 4 | N-(2-(6-fluoro-7-methoxy-naphthalen-1-yl)ethyl)acetamide | |
| 5 | N-(2-(6-chloro-7-deuteromethoxy-naphthalen-1-yl)ethyl)propanamide | |
| 6 | N-(2-(6-chloro-7-methoxy-naphthalen-1-yl)ethyl)propanamide | |
| 7 | N-(2-(6-fluoro-7-methoxy-naphthalen-1-yl)ethyl)propanamide | |
| 8 | A hydrogen chloride/water complex of Example 1 | HCl · xH$_2$O |

TABLE 1-continued

Example compounds

| Number | Compound name | Structural formula |
|---|---|---|
| 9 | A hydrogen chloride complex of Example 1 | 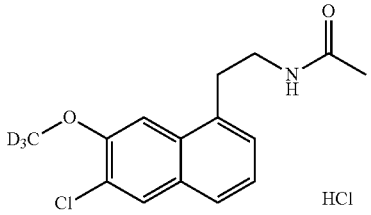 [SMILES: [2H]C([2H])([2H])Oc1cc2c(CCNC(C)=O)cccc2cc1Cl ; Cl] HCl |
| 10 | A hydrogen chloride/water complex of Example 2 | 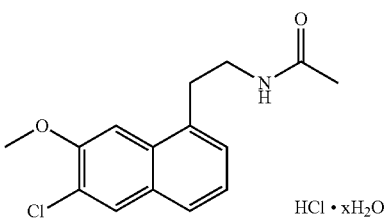 HCl • xH$_2$O |
| 11 | A hydrogen chloride complex of Example 2 | 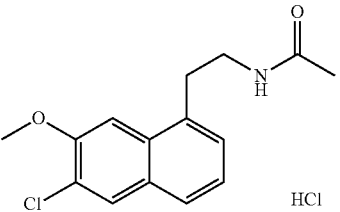 [SMILES: COc1cc2c(CCNC(C)=O)cccc2cc1Cl ; Cl] HCl |
| 12 | A hydrogen bromide/water complex of Example 2 | 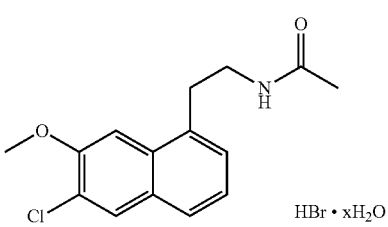 [SMILES: COc1cc2c(CCNC(C)=O)cccc2cc1Cl ; "HBr · xH2O"] HBr • xH$_2$O |
| 13 | A sulfuric acid complex of Example 2 | 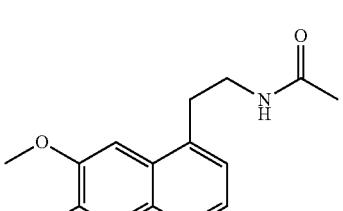 H$_2$SO$_4$ |
| 14 | A methanesulfonic acid complex of Example 2 | 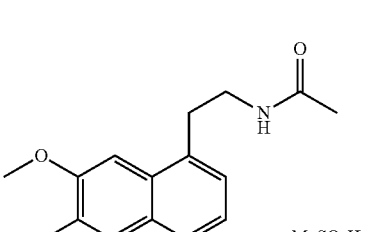 MeSO$_3$H |

TABLE 1-continued

Example compounds

| Number | Compound name | Structural formula |
|---|---|---|
| 15 | A hydrogen chloride/water complex of Example 4 | 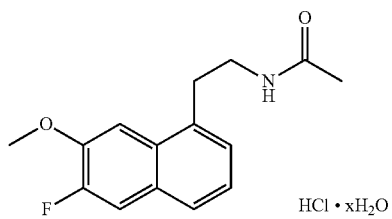 [SMILES: COc1cc2c(CCNC(C)=O)cccc2cc1F ; "HCl · xH2O"] HCl • xH₂O |
| Control | d3-Agomelatine | 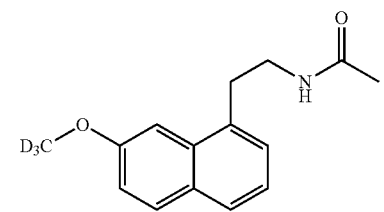 [SMILES: [2H]C([2H])([2H])Oc1ccc2cccc(CCNC(C)=O)c2c1] |

In the present application, when the name of a compound is inconsistent with a structural formula, the structural formula shall prevail.

At least one embodiment disclosed herein provides a pharmaceutical agent as a melatonin receptor agonist comprising a compound disclosed herein as an active ingredient.

At least one embodiment disclosed herein provides a pharmaceutical agent as a 5-HT$_{2C}$ receptor antagonist comprising a compound disclosed herein as an active ingredient.

At least one embodiment disclosed herein provides a pharmaceutical agent that acts both as a melatonin receptor agonist and as a 5-HT$_{2C}$ receptor antagonist, comprising a compound disclosed herein as an active ingredient.

The compound disclosed herein is useful for preventing or treating a melatoninergic system disease, stress, anxiety, a seasonal affective disorder, a cardiovascular disease, a digestive system disease, schizophrenia, phobia, depression, major depression; a sleep disorder, dyssomnia, insomnia or fatigue due to jet-lag; or body weight deregulation in a subject, including a human and mammal. For example, a compound of any one of the above-mentioned embodiments disclosed herein, or a pharmaceutically acceptable salt or solvate thereof, or a mixture thereof, is useful for preventing or treating a disease or condition selected from the group consisting of depression, anxiety, dyssomnia, and body weight deregulation in a subject in need thereof.

At least one embodiment disclosed herein provides a method for producing a pharmaceutical composition comprising admixing at least one compound of any one of compound embodiments disclosed herein with a pharmaceutically acceptable adjuvant.

The compound disclosed herein may be formulated into a pharmaceutical formulation, including dosage forms suitable for oral administration for example, as tablet, pill, syrup, powder, granule or capsule, for parenteral injection (e.g., intravenous injection, subcutaneous injection) for example, as a solution, for topical administration for example, as ointment, patch or cream, and for rectal administration for example, as suppository.

Depending on a disease and patient to be treated and a route of administration, a pharmaceutical formulation disclosed herein may be administered one or more times daily at different doses. For example, a daily dose of a compound disclosed herein may be about 0.1-0.4 mg/kg body weight for oral administration.

In certain aspects, a compound disclosed herein may be administered alone or in combination with other compounds, including other melatonin receptor agonists or other 5-HT$_{2C}$ receptor antagonists or other therapeutic agents. For example, a compound disclosed herein can be administered in combination with one or more drugs selected from the group consisting of Melatonin, Agomelatine, Ramelteon, and Tasimelteon. The term "pharmaceutical combination" or "administration in combination" as used herein may encompass simultaneous or sequential administration.

At least one embodiment disclosed herein provides a method for preparing a compound disclosed herein, or a pharmaceutically acceptable salt or solvate thereof, or a mixture thereof, as described above.

An exemplary reaction scheme (taking Examples 1, 2, and 8 as an example):

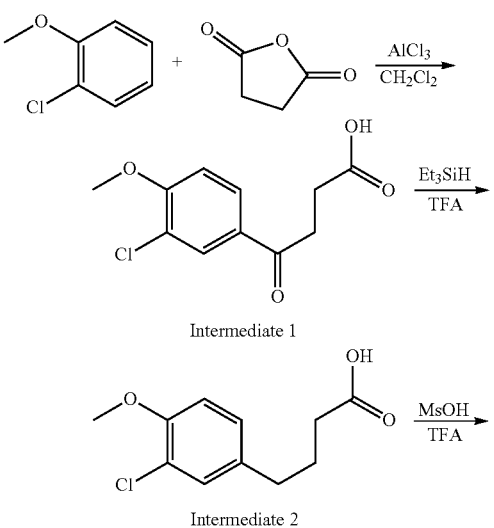

Intermediate 1

Intermediate 2

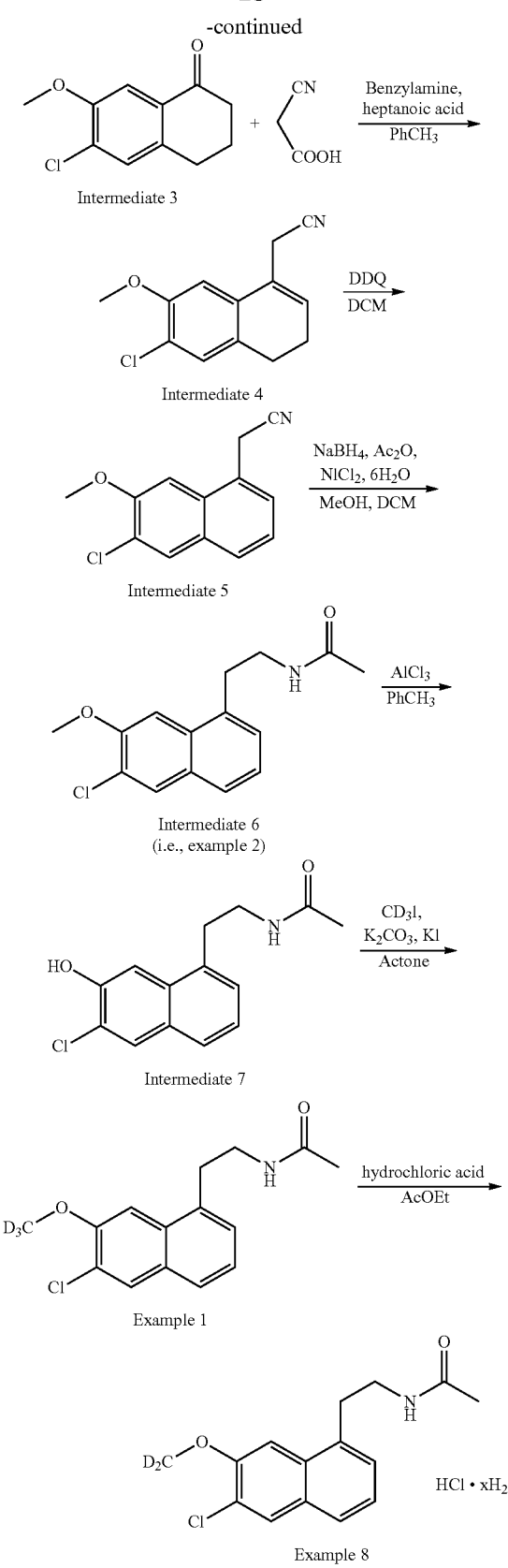

At least one embodiment disclosed herein provides a method for synthesizing a compound of formula I, comprising:

carrying out a Friedel-Crafts reaction between methoxybenzene or methoxybenzene ortho-substituted with halogen and succinic anhydride under the action of a catalyst to give an aromatic ketone, i.e., intermediate 1;

reducing a carbonyl group of ketone in the intermediate 1 to a methylene group with triethylsilane to give an intermediate 2;

cyclizing the intermediate 2 under the action of an acidic catalyst to give tetralin, i.e., intermediate 3;

cyanating the intermediate 3 with cyanoacetic acid to give dihydronaphthylacetonitrile, i.e., intermediate 4;

dehydrogenating the intermediate 4 to give naphthylacetonitrile, i.e., intermediate 5; and reacting the intermediate 5 with sodium borohydride and acetic anhydride/propionic anhydride in the presence of a catalyst nickel chloride hexahydrate to give an acetamide/propionamide compound.

In at least one embodiment disclosed herein, the synthesis method may further comprise:

dissolving the acetamide/propionamide compound as described above in toluene to react with anhydrous aluminum trichloride to give a naphthol; and reacting the naphthol with deuterated methyl iodide to give a deuterated acetamide/propionamide compound.

In at least one embodiment disclosed herein, the synthesis method may further comprise:

reacting the acetamide/propionamide compound or the deuterated acetamide/propionamide compound as described above with an acid to form a salt.

For specific operations, for example, reference may be made to the description section of the examples.

Based on the detailed teachings disclosed herein and the existing synthetic common sense, those skilled in the art can readily synthesize the compounds of formula I disclosed herein.

At least one embodiment disclosed herein provides a pharmaceutical composition comprising:

a therapeutically and/or prophylactically effective amount of a compound of any one of the embodiments disclosed herein, or a pharmaceutically acceptable salt or solvate thereof or a mixture thereof, and optionally a pharmaceutically acceptable adjuvant.

At least one embodiment disclosed herein provides a method for preventing or treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation, the method comprising administering a pharmaceutical composition disclosed herein to a subject in need thereof.

At least one embodiment disclosed herein provides use of a compound disclosed herein, or a pharmaceutically acceptable salt or solvate thereof, or a mixture thereof, for treating a disease or condition selected from the group consisting of melatoninergic system disease, stress, anxiety, seasonal affective disorder, cardiovascular disease, digestive system disease, schizophrenia, phobia, depression, major depression; sleep disorder, dyssomnia, insomnia or fatigue due to jet-lag; or body weight deregulation.

In the context disclosed herein, the following abbreviations are used:

TLC: thin layer chromatography;
DDQ: 2,3-dichloro-5,6-dicyano-1,4-benzoquinone;
TFA: trifluoroacetic acid;
DMSO: dimethyl sulfoxide.

The embodiments disclosed herein will be described in detail below with reference to the examples disclosed herein, but it is to be understood for those skilled in the art that the following examples are intended to illustrate the present disclosure and not to limit the scope of the present disclosure.

Examples that do not indicate specific conditions are carried out according to conventional conditions or conditions recommended by the manufacturer. Reagents or instruments that do not indicate manufacturers are conventional products that can be purchased from the market.

Part I: Synthesis of Example Compounds

Synthesis of Example 1 and Examples 2 and 8

The reaction route is as above, and the specific synthesis operation is as follows:

Intermediate 1

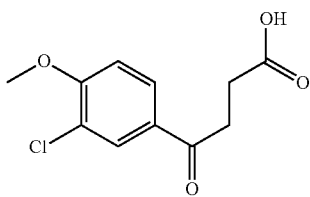 [SMILES: COc1ccc(C(=O)CCC(=O)O)cc1Cl]

A 3 liter three-necked bottle was equipped with a condensing tube. 328 g (2.46 mol) of aluminum trichloride was added to 1.7 liters of dichloromethane under an ice bath, and completely dissolved with stirring. To the solution were added 156.8 g (138 mL, 1.10 mol) of o-chloroanisole in one portion, and then 123 g (1.23 mol) of succinic anhydride in batches. The system exothermed and produced gas, and spontaneous reflux occurred. After the end of the spontaneous reflux, the system was heated to reflux. After refluxing for 2 hours, the progress of the reaction was monitored by TLC. If the starting material disappeared, the reaction can be stopped. After naturally cooling, the mixture was poured into 5 liters of ice water. The mixture was acidified with 300 ml of concentrated hydrochloric acid with stirring, and a large amount of solid appeared in the system. After stirring for half an hour, the mixture was filtered. The filter cake was washed with 1 liter of water and then recrystallized from ethanol/water to give a white or pale pink powder. Yield: 79.2%, m.p.: 186-188° C.

$^1$H-NMR (400 MHz, DMSO-d6), δ: 2.54-2.57 (t, 2H, J=6.16 Hz), 3.19-3.23 (t, 2H, J=6.20 Hz), 3.95 (s, 3H), 7.27-7.29 (d, 1H, J=9.24 Hz), 7.97-8.00 (m, 2H), 12.16 (s, 1H).

Intermediate 2

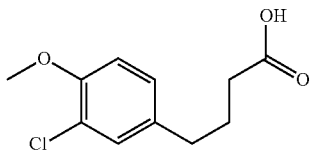

121.4 g (0.5 mol) of the intermediate 1 was added to a 1 liter eggplant-shaped flask, and then 270 ml of trifluoroacetic acid and 180 ml of triethylsilane were further added thereto. The mixture was stirred under reflux. After refluxing for 5 hours, the progress of the reaction was monitored by TLC. If the starting material disappeared, the reaction can be stopped. The system was rotary evaporated to no significant solvent distillation. To the residue was added 1 liter of ethyl acetate. The mixture was washed 3 times with 500 ml of water and then twice with 300 ml of a 3 mol/L aqueous NaOH solution. The aqueous phases of NaOH were combined and acidified with 6 mol/L hydrochloric acid under ice bath to give a large amount of white precipitate. The precipitate was filtered, and the cake was dried to give a crude product in a yield of 94.6%. The crude product can be directly used in the next step, or can be recrystallized from ethyl acetate/cyclohexane to give a colorless crystal. M.p.: 63-66° C.

$^1$H-NMR (400 MHz, DMSO-d6), δ: 1.73-1.79 (m, 2H), 2.16-2.20 (t, 2H, J=7.28 Hz), 2.51-2.54 (m, 2H), 3.81 (s, 3H), 7.04-7.06 (d, 1H, J=8.44 Hz), 7.10-7.13 (dd, 1H, J$_1$=8.40 Hz, J$_2$=1.88 Hz), 7.24-7.25 (d, 1H, J=1.96 Hz), 12.15 (s, 1H).

Intermediate 3

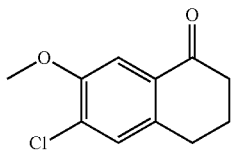

To 113 g of the intermediate 2 were added 480 ml of trifluoroacetic acid and 120 ml of methanesulfonic acid. After mixing and heating under reflux for 7 hours, the progress of the reaction was monitored by TLC. If the starting material disappeared, the reaction can be stopped. After cooling, the mixture was poured into 2.5 liters of ice water and stirred, and a large amount of pale yellow solid appeared. The solid was filtered and washed with water. The filter cake was recrystallized from ethanol/water to give a pale yellow crystal in a yield of 75.6%. M.p.: 105-108° C.

$^1$H-NMR (400 MHz, CDCl$_3$), δ: 2.09-2.16 (m, 2H), 2.62-2.65 (t, 2H, J=6.8 Hz), 2.87-2.90 (t, 2H, J=6.2 Hz), 3.94 (s, 3H), 7.28 (s, 1H), 7.56 (s, 1H).

Intermediate 4

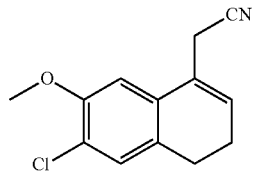 [SMILES: COc1cc2c(cc1Cl)CCC=C2CC#N]

To a 1 liter three-necked flask were added 75.0 grams of intermediate 3, 45.6 grams of cyanoacetic acid, 10 grams of benzylamine, 12 grams of heptanoic acid, and 700 milliliters of toluene. A water separator was added. The mixture was refluxed at an external temperature of 140° C. and water was separated. The reaction was completed by TLC monitoring after 24 hours. After cooling, the mixture was washed twice with water, and the insoluble material was filtered off. The solvent was rotary evaporated to dryness and the residue was recrystallized from ethanol/water to give a pale yellow crystal. Yield: 88.3%, m.p.: 100-104° C.

$^1$H-NMR (400 MHz, DMSO-d6), δ: 2.31-2.36 (m, 2H), 2.69-2.73 (t, 2H, J=8.26 Hz), 3.49 (s, 2H), 3.92 (s, 3H), 6.26-6.28 (t, 1H, J=4.34 Hz), 6.69 (s, 1H), 7.18 (s, 1H).

Intermediate 5

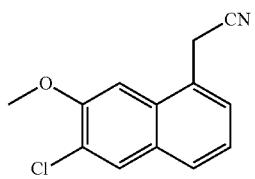 [SMILES: COc1cc2c(CC#N)cccc2cc1Cl]

70.1 g of the intermediate 4 was dissolved in 900 ml of dichloromethane. To the mixture was added 75 g (0.33 mol) of DDQ in batches under cooling and the internal temperature was controlled to not exceed 20° C. After the addition was completed, the system became black. The mixture was reacted at about 20° C. for 30 min, and the reaction was completed by TLC monitoring. The solid was removed by filtration, and the filtrate was washed twice with a saturated aqueous solution of sodium carbonate (400 ml) to colorless, and washed once with 300 ml of saturated brine. The organic phase was dried over anhydrous sodium sulfate. After filtering, the solvent was rotary evaporated to dryness. The residue was recrystallized from cyclohexane/ethyl acetate to give a white crystal. Yield: 90.7%, m.p.: 140-144° C.

$^1$H-NMR (400 MHz, CDCl3), δ: 4.05 (s, 2H), 4.08 (s, 3H), 7.12 (s, 1H), 7.35-7.39 (dd, 1H, $J_1$=8.14, $J_2$=7.28), 7.54-7.56 (d, 1H, J=7.24), 7.72-7.74 (d, 1H, J=8.12), 7.93 (s, 1H).

Intermediate 6 (i.e., Example 2)

N-(2-(6-chloro-7-methoxy-naphthalen-1-yl)ethyl)acetamide

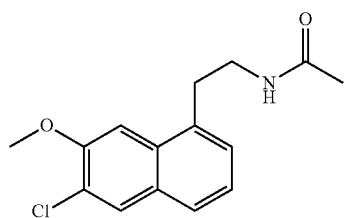 [SMILES: COc1cc2c(CCNC(C)=O)cccc2cc1Cl]

36.0 g of the intermediate 5 was dissolved in a mixed solution of 700 ml of anhydrous methanol and 1300 ml of dichloromethane. To the mixture was added 23 g of nickel chloride hexahydrate under cooling at −10° C., and all of them were dissolved by stirring. Further, to the mixture were added 35 ml of acetic anhydride, and then 26.4 g of sodium borohydride in batches. The rate of addition was controlled so that the internal temperature was between 0 and 10° C. After the addition was completed, the mixture was stirred at room temperature for 3 hours, and the reaction was completed by TLC monitoring. To the mixture was added 500 ml of 3 mol/L hydrochloric acid under cooling with ice bath, and was stirred for 1 hour. The organic solvent was removed again by rotary evaporation. To the residue was added 1 liter of ethyl acetate. The mixture was washed successively with 500 ml of water, a saturated aqueous solution of sodium hydrogen carbonate and a saturated aqueous solution of sodium chloride. The organic phase was dried over anhydrous sodium sulfate and filtered. The filtrate was further added with 4.3 g of activated carbon, boiled for 30 minutes, and then filtered. The filtrate was rotary evaporated to dryness, and treated with cyclohexane/ethyl acetate to give a white solid. Yield: 72.1%, m.p.: 142-145° C.

$^1$H-NMR (400 MHz, DMSO-d6), δ: 1.83 (s, 3H), 3.11-3.15 (m, 2H), 3.30-3.34 (m, 2H), 4.05 (s, 3H); 7.30-7.36 (m, 2H); 7.70-7.72 (d, 1H, J=7.60 Hz); 7.79 (s, 1H); 8.07 (s, 1H); 8.14-8.17 (t, 1H, J=5.60 Hz). ESI-MS m/e: 278.1 ([M+1]±).

Intermediate 7

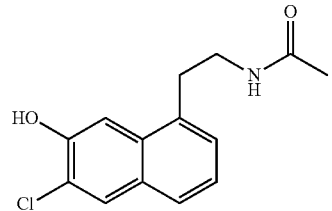 [SMILES: CC(=O)NCCc1cccc2cc(Cl)c(O)cc12]

23.5 g of the intermediate 6 was dissolved in 1000 ml of toluene, and then 25.2 g of anhydrous aluminum trichloride was added thereto. After refluxing for 1.5 hours, the reaction was completed by TLC monitoring. After cooling, toluene was poured off, and to the residue was added 600 ml of ethyl acetate. The mixture was washed successively with 300 ml of a saturated aqueous solution of sodium hydrogen carbonate and a saturated aqueous solution of sodium chloride. The organic phase was dried over anhydrous sodium sulfate. After filtration, the solvent was rotary evaporated to dryness, and treated with cyclohexane/ethyl acetate to give a pale yellow solid. Yield: 82.0%, m.p.: 174-176° C.

$^1$H-NMR (400 MHz, DMSO-d6), δ: 1.80 (s, 3H), 3.10-3.14 (t, 2H, J=7.28 Hz), 3.33-3.38 (m, 2H), 7.23-7.28 (m, 2H), 7.49 (s, 1H), 7.65-7.68 (dd, 1H, $J_1$=7.32 Hz, $J_2$=2.28 Hz), 7.98-8.02 (m, 2H), 10.52 (s, 1H).

Example 1: N-(2-(6-chloro-7-deuteromethoxy-naphthalen-1-yl)ethyl)acetamide

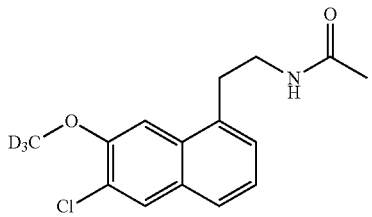

17.3 g of the intermediate 7 was dissolved in 1 liter of acetone, and then 27.2 g of potassium carbonate, 1.3 g of potassium iodide, and 12.4 g (5.31 ml) of deuterated iodomethane were added thereto. After reacting at room temperature for 24 hours, the reaction was completed by TLC monitoring. The mixture was filtered, and the filtrate was rotary evaporated to dryness. To the residue was added 400 ml of ethyl acetate, and the mixture was washed successively with 200 ml of water and a saturated aqueous solution of sodium chloride. The organic phase was dried over anhydrous sodium sulfate and filtered. The filtrate was further added with 2 g of activated carbon, boiled for 30 minutes, filtered, and rotary evaporated to dryness. The residue was treated with cyclohexane/ethyl acetate to give a white powdery solid. Yield: 81.4%, m.p.: 148-151° C.

$^1$H-NMR (400 MHz, DMSO-d6), δ: 1.83 (s, 3H), 3.11-3.20 (m, 2H), 3.29-3.35 (m, 2H), 7.30-7.36 (m, 2H), 7.70-7.72 (dd, 1H, $J_1$=7.80 Hz, $J_2$=1.40 Hz), 7.80 (s, 1H), 8.07 (s, 1H), 8.15-8.18 (t, 1H, J=5.46 Hz). ESI-MS m/e: 281.1 ([M+1]±).

Example 8

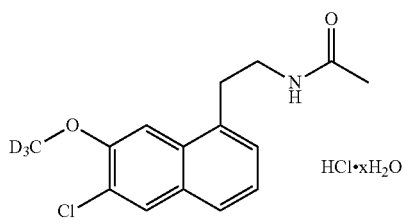 [SMILES: [2H]C([2H])([2H])Oc1cc2c(CCNC(C)=O)cccc2cc1Cl]

Under ice bath, 1.0 g of Example 1 was dissolved in 30 ml of ethyl acetate, and 0.50 ml of concentrated hydrochloric acid was added thereto. After stirring for 1 hour, a large amount of white solid was precipitated. The solid was filtered, washed with 10 ml of cold ethyl acetate, and dried to give a white solid (0.89 g) in a yield of 78.8%. M.p.: 102-105° C. $^1$H-NMR (400 MHz, DMSO-d6), δ: 1.83 (s, 3H), 3.11-3.20 (m, 2H), 3.29-3.35 (m, 2H), 7.30-7.36 (m, 2H), 7.70-7.72 (dd, 1H, $J_1$=7.80 Hz, $J_2$=1.40 Hz), 7.80 (s, 1H), 8.07 (s, 1H), 8.15-8.18 (t, 1H, J=5.46 Hz). (The hydrogen spectrum data is actually the same as in Example 1, and only the water peak position and area are different).

Synthesis of Examples 3 and 4

The synthesis was the same as the synthesis of Examples 1 and 2 except that the starting material was replaced with o-fluoroanisole.

Example 3

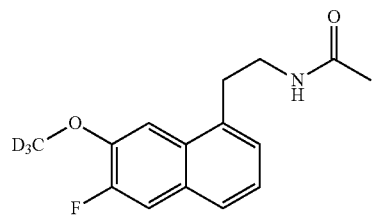 [SMILES: [2H]C([2H])([2H])Oc1cc2c(CCNC(C)=O)cccc2cc1F]

White solid, m.p.: 141-144° C. $^1$H-NMR (400 MHz, DMSO-d6), δ: 1.83 (s, 3H), 3.10-3.14 (m, 2 Hz), 3.29-3.35 (m, 4H), 7.31-7.32 (m, 2H), 7.68-7.71 (m, 1H), 7.72-7.75 (d, 1H, J=12.32 Hz), 7.82-7.85 (d, 1H, J=8.96 Hz), 8.15-8.18 (t, 1H, J=5.62 Hz). ESI-MS m/e: 265.1 ([M+1]±).

Example 4: N-(2-(6-fluoro-7-methoxy-naphthalen-1-yl)ethyl)acetamide

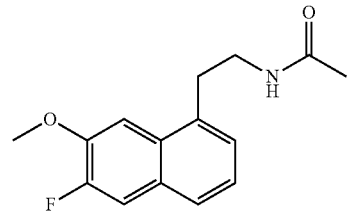

White solid, m.p.: 140-144° C. $^1$H-NMR (400 MHz, DMSO-d6), δ: 1.83 (s, 3H), 3.11-3.15 (m, 2 Hz), 3.29-3.36 (m, 4H), 4.05 (s, 3H), 7.30-7.32 (m, 2H), 7.69-7.72 (m, 1H), 7.73-7.76 (d, 1H, J=12.44 Hz), 7.82-7.85 (d, 1H, J=8.98 Hz), 8.16-8.19 (t, 1H, J=5.54 Hz). ESI-MS m/e: 262.1 ([M+1]±).

Synthesis of Examples 5 and 6

The synthesis was the same as the synthesis of Examples 1 and 2 except that acetic anhydride was replaced with propionic anhydride in the sixth step of synthesis.

Example 5: N-(2-(6-chloro-7-deuteromethoxy-naphthalen-1-yl)ethyl)propanamide

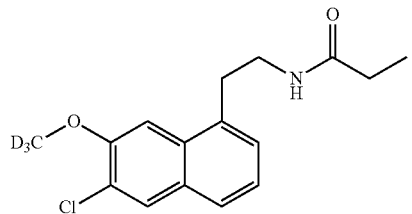 [SMILES: [2H]C([2H])([2H])Oc1cc2c(CCNC(=O)CC)cccc2cc1Cl]

White solid. $^1$H-NMR (400 MHz, DMSO-d6), δ: 1.00-1.03 (t, 3H, J=7.56 Hz), 2.07-2.12 (q, 2H, J=7.56 Hz), 3.12-3.17 (m, 2H), 3.32-3.38 (m, 2H), 7.32-7.38 (m, 2H), 7.72-7.74 (dd, 1H, $J_1$=6.88 Hz, $J_2$=1.92 Hz), 7.77 (s, 1H), 8.01-8.03 (t, 1H, J=5.60 Hz), 8.07 (s, 1H). ESI-MS m/e: 295.1 ([M+1]±).

Example 6: N-(2-(6-chloro-7-methoxy-naphthalen-1-yl)ethyl)propanamide

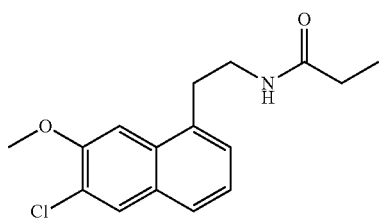 [SMILES: CCC(=O)NCCc1cccc2cc(Cl)c(OC)cc12]

White solid. $^1$H-NMR (400 MHz, DMSO-d6), δ: 0.99-1.02 (t, 3H, J=7.60 Hz), 2.06-2.11 (q, 2H, J=7.60 Hz), 3.12-3.16 (m, 2H), 3.31-3.37 (m, 2H), 4.05 (s, 3H), 7.30-7.36 (m, 2H), 7.70-7.72 (dd, 1H, $J_1$=7.12 Hz, $J_2$=1.96 Hz), 7.76 (s, 1H), 8.00-8.02 (t, 1H, J=5.50 Hz), 8.06 (s, 1H). ESI-MS m/e: 292.1 ([M+1]±).

Example 7: N-(2-(6-fluoro-7-methoxy-naphthalen-1-yl)ethyl)propanamide

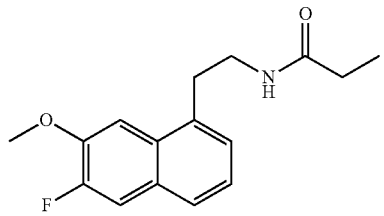 [SMILES: CCC(=O)NCCc1cccc2cc(F)c(OC)cc12]

The same procedure as in Example 4 was carried out except that acetic anhydride was replaced with propionic anhydride in the sixth step of synthesis. White solid, $^1$H-NMR (400 MHz, DMSO-d6), δ: 0.98-1.01 (t, 3H, J=7.52 Hz), 2.05-2.10 (q, 2H, J=7.52 Hz), 3.10-3.14 (m, 2 Hz), 3.28-3.35 (m, 4H), 4.04 (s, 3H), 7.30-7.32 (m, 2H), 7.68-7.71 (m, 1H), 7.73-7.76 (d, 1H, J=12.52 Hz), 7.81-7.84 (d, 1H, J=9.02 Hz), 8.02-8.04 (t, 1H, J=5.58 Hz). ESI-MS m/e: 276.1 ([M+1]±).

Synthesis of Examples 9-15

The synthesis of Examples 9-15 was the same as that of Example 8. 1.0 g of the corresponding example compound was dissolved in 30 ml of ethyl acetate under ice-bath, and then a certain amount of acid was added thereto respectively. The mixture was stirred and precipitated. The precipitated solid was filtered, and washed with ethyl acetate to give a white solid. If a mineral acid (HCl/HBr/H$_2$SO$_4$ or the like) was used, the $^1$H-NMR of the new example was completely identical to the original example except that the water peak area and position was slightly different, which will not be repeated in the following examples; if an organic acid was used, the $^1$H-NMR of the new example was different from that of the original example. The specific operations and data were as follows:

Example 9

1.0 g of Example 1, 2 ml of a 3.5 mol/L anhydrous HCl/ethyl acetate solution was added. M.p.: 106-108° C., yield: 77.8%.

Example 10

1.0 g of Example 2, 0.50 ml of concentrated hydrochloric acid was added. M.p.: 100-103° C., yield: 82.3%.

Example 11

1.0 g of Example 2, 2 ml of a 3.5 mol/L HCl/ethyl acetate solution was added. M.p.: 104-107° C., yield: 80.5%.

Example 12

1.0 g of Example 2, 0.61 ml of a 40% aqueous solution of HBr was added. M.p.: 145-151° C., yield: 76.9%.

Example 13

1.0 g of Example 2, 0.23 ml of concentrated sulfuric acid was added. M.p.: 186-190° C., yield: 92.1%.

Example 14

1.0 g of Example 2, 0.25 ml of methanesulfonic acid was added. M.p.: 156-159° C., yield: 68.4%. $^1$H-NMR (400 MHz, DMSO-d6), δ: 1.84 (s, 3H), 2.33 (s, 3H), 3.13-3.17 (m, 2H), 3.31-3.36 (m, 2H), 4.06 (s, 3H); 7.32-7.38 (m, 2H); 7.72-7.74 (d, 1H, J=7.28 Hz); 7.81 (s, 1H); 8.09 (s, 1H); 8.16-8.19 (t, 1H, J=5.44 Hz).

Example 15

1.0 g of Example 4, 0.50 ml of concentrated hydrochloric acid was added. M.p.: 104-107° C., yield: 76.2%.

Synthesis of Control d3-Agomelatine

The control was a known compound and used as a reference for activity evaluation. It was synthesized in the same manner as in Example 1, except that the intermediate 6 was replaced with Agomelatine. White solid, m.p.: 95-97° C. $^1$H-NMR (400 MHz, DMSO-d6), δ: 1.83 (s, 3H); 3.10-3.14 (m, 2H); 3.30-3.35 (m, 2H); 7.15-7.18 (dd, 1H, $J_1$=8.60 Hz; $J_2$=2.44 Hz); 7.24-7.32 (m, 2H); 7.61-7.60 (d, 1H, J=2.52 Hz); 7.70-7.72 (d, 1H, J=7.84 Hz); 7.81-7.83 (d, 1H, J=8.96 Hz); 8.11-8.14 (t, 1H, J=5.60 Hz).

Part II: In Vitro Receptor Binding Test of Example Compounds

The example compounds were subjected to an in vitro receptor binding test using Agomelatine (abbreviated as Ago) and d3-Agomelatine (abbreviated as d3-Ago) as controls to evaluate the competitive binding ability of the test compounds and the radioligand to receptors in vitro. The receptors included a MT$_1$/MT$_2$ receptor and a 5-HT$_{2C}$ receptor. The test was divided into two parts: prescreening and rescreening. The results of prescreening were expressed as the percentage of binding, and the results of rescreening were expressed as the IC$_{50}$ value (in M, i.e., mol/L).

Test Materials and Reagents (1) The human MT$_1$/MT$_2$ receptor membrane proteins were PerkinElmer's products ES-620 (MT$_1$) and ES-621 (MT$_2$); the 5-HT$_{2C}$ receptor membrane protein was extracted from rat hippocampus and stably transfected HEK293 cell line according to the method for nucleus-cytoplasm-membrane preparation kit of Applygen Technologies Inc.

(2) The labeled ligand used in the test was available from PE Inc, and the unlabeled ligand was available from Sigma Inc; phenylmethylsulfonyl fluoride (PMSF) was available from Sigma Inc; the scintillation liquid was available from PE Inc; the Folin-phenol reagent was available from HAWI Science & Technology CO., LTD; and other reagents were of analytical grade purity.

(3) Tris-HCl buffer formulation: 50 mM Tris-HCl Buffer, 1 mM EDTA, 5 mM MgCl$_2$, 0.1% NaN3, and then a certain proportion of PMSF was added to make pH 7.4.

(4) The example compound to be tested was dissolved in DMSO and formulated as a stock solution of $10^{-2}$ M, and then diluted with distilled water to a concentration gradient of $10^{-4}$-$10^{-11}$ M. The prescreening of the MT receptor binding test was performed at the concentration of $10^{-5}$ M; the prescreening of the 5-HT$_{2C}$ receptor binding test was performed at the concentrations of $10^{-5}$ and $10^{-7}$ M.

Data Processing and Statistical Analysis

The statistical analysis was performed using GraphPad Prism 5.0 software. The formula for receptor binding test was: inhibition (%)=[(total CPM of binding−CPM of tube with drug)/(total CPM of binding−non-specific CPM)]× 100%, wherein CPM was count of a radioactive intensity. The logarithmic concentrations of the test compounds were nonlinearly fitted at a percentage of specific binding to give a competitive inhibition curve, and the IC$_{50}$ value was calculated.

1. MT$_1$/MT$_2$ Receptor Binding Test

The test tubes were placed in a reaction condition of 25° C. 10 μL of receptor membrane protein MT$_1$ or MT$_2$ was added to all the tubes. In non-specific binding tubes, 50 μL of a corresponding unlabeled ligand Ago at a concentration of $10^4$ M was added to a final concentration of 10 μM, and pre-reacted for 30 minutes. In test tubes, 30 μL of test drug (MT$_1$: a concentration of $10^4$-$10^{-10}$ M, MT$_2$: a concentration of $10^4$-$10^{-11}$ M) was added, respectively; all tubes were added with 40 μL [$^3$H]-Melotonin, respectively. The volume in all reaction tubes was made up to 300 μL with Tris-HCl buffer (50 mM Tris-HCl, 1 mM EDTA, 5 mM MgCl$_2$, 0.1 mM PMSF, 0.1% NaN3, pH 7.4); the reaction was carried out at 25° C. for 1 hour; the mixture was then spotted on a type 49 glass fiber filter paper, suction filtered under a vacuum, washed 3 times with 2 mL of ice-cold Tris-HCl buffer (50 mM Tris-HCl Buffer, 1 mM EDTA, 5 mM MgCl$_2$, 0.1% NaN3, pH7.4), and dried with suction. The filter paper was taken out and dried by baking, and then placed in a scintillation bottle. 1 mL of the scintillation liquid was added, and the radioactive intensity was measured by a liquid scintillation counter.

According to the formula, the percentage of binding was measured, and the value of IC$_{50}$ was further obtained. The test results were shown in Table 2.

TABLE 2

Prescreening ($10^{-5}$ M) and rescreening results of MT$_1$/MT$_2$ receptor binding of Example compounds

| Compound | MT$_1$ binding ratio (I %) | Rescreening IC$_{50}$(nM) | MT$_2$ binding ratio (I %) | Rescreening IC$_{50}$(nM) |
|---|---|---|---|---|
| Ago | 80 | 0.69 ± 0.21 | 88 | 0.99 ± 0.14 |
| d3-Ago | 50 | | 45 | |
| Example 1 | 84 | 0.45 ± 0.26 | 98 | 0.72 ± 0.13 |
| Example 2 | 84 | | 78 | |
| Example 3 | 66 | | 57 | |
| Example 4 | 77 | 0.23 ± 0.24 | 84 | 0.67 ± 0.08 |
| Example 5 | 81 | | 44 | |
| Example 6 | 77 | | 36 | |
| Example 7 | 73 | | 69 | |

2. 5-HT$_{2C}$ Receptor Binding Test

The test tubes were placed under a reaction condition of 25° C. 50 μg of the receptor membrane protein 5-HT$_{2C}$ was added to all the tubes. In non-specific binding tubes, 50 μL of a corresponding unlabeled ligand 5-HT at a concentration of $10^{-4}$ M was added to a final concentration of 10 μM, and pre-reacted for 30 minutes. In test tubes, 30 μL of test example compounds (a concentration of $10^4$-$10^{-10}$ M) were added, respectively. All tubes were added with 40 μL of [$^3$H]-LSD (lysergic acid diethylamide), respectively. The volume in all reaction tubes was made up to 300 μL with Tris-HCl buffer (50 mM Tris-HCl, 1 mM EDTA, 5 mM MgCl$_2$, 0.1% NaN3, 0.1 mM PMSF, pH 7.4); the reaction was carried out at 25° C. for 1 hour; the mixture was then spotted on a type 49 glass fiber filter paper, suction filtered under a vacuum, washed 3 times with 2 mL of ice-cold Tris-HCl buffer (50 mM Tris-HCl Buffer, 1 mM EDTA, 5 mM MgCl$_2$, 0.1% NaN3, pH7.4), and dried with suction. The filter paper was taken out and dried by baking, and then placed in a scintillation bottle. 1 mL of the scintillation liquid was added, and the radioactive intensity was measured by a liquid scintillation counter.

According to the formula, the percentage of binding was measured, and the value of IC$_{50}$ was further obtained. The test results were shown in Table 3.

TABLE 3

Screening results of 5-HT$_{2C}$ receptor binding of Example compounds

| Compound | Prescreening, 5-HT$_{2C}$ receptor binding ratio (%) | | Rescreening |
| | $10^{-5}$ M | $10^{-7}$ M | IC$_{50}$(nM) |
|---|---|---|---|
| Ago | 100 | 72 | 4.52 ± 0.25 |
| d3-Ago | 65 | 32 | |
| Example 1 | 94 | 85 | 0.77 ± 0.018 |
| Example 2 | 82 | 56 | |
| Example 3 | 100 | 67 | |
| Example 4 | 100 | 78 | 20.79 ± 2.45 |
| Example 5 | 92 | 73 | |
| Example 6 | 88 | 70 | |
| Example 7 | 92 | 68 | |

The in vitro receptor binding test of some of the example compounds were graphically illustrated in FIG. 1.

Part III: Study on Metabolism of Example Compounds

The metabolic stability of the example compounds was evaluated by in vitro (human liver microsome incubation system) and in vivo (rat oral/tail vein injection model) tests.

Test Materials and Reagents

Human liver microsomes (BD Gentest Inc, Cat. No. 452161); acetonitrile, aconitine, and verapamil from Sigma Inc; NADPH (reduced coenzyme II) from Roche Inc; 0.1 M pH 7.4 PBS (phosphate buffer, home-made); other reagents are of analytical grade.

Male SD rats, weighing 200±20 g, SPF grade, were purchased from SPF Biotechnology Co., Ltd.

Instruments, Conditions and Parameters

TSQ Quantum liquid chromatography-mass spectrometer (LC/MS/MS) from Finnigan Inc, USA, chromatography column: TSKgel Amide-80 column (2.0 mm I.D.×100 mm, 5 μm); mobile phase: acetonitrile-water-formic acid (50:50:0.1); flow rate: 0.2 mL/min; injection volume: 5 μL; column temperature: room temperature. Ionization source is electrospray ionization (ESI) with 4.8 KV of spray voltage; capillary temperature (TEM): 300° C.; sheath gas: N2, flow rate: 10 psi; auxiliary gas: N2, flow rate: 1 psi; collision gas (CID): Ar at a pressure of 1.5 mTorr. The mass spectrometry scanning method was selective reaction monitoring (SRM) and detected by positive ion method. The internal standard was a 0.2 m/mL solution of aconitine in acetonitrile, the minimum limit of quantification was 5 ng/mL, and the correlation coefficient was >0.99.

1. In Vitro Metabolism Study

Verapamil was used as a reference to verify the detection system. In an in vitro test of a human liver microsomal incubation system, using Agomelatine (Ago) and d3-Agomelatine (d3-Ago) as references, the reduction rate of concentration of each example compound was observed to evaluate the metabolic stability in vitro.

Figure 2:
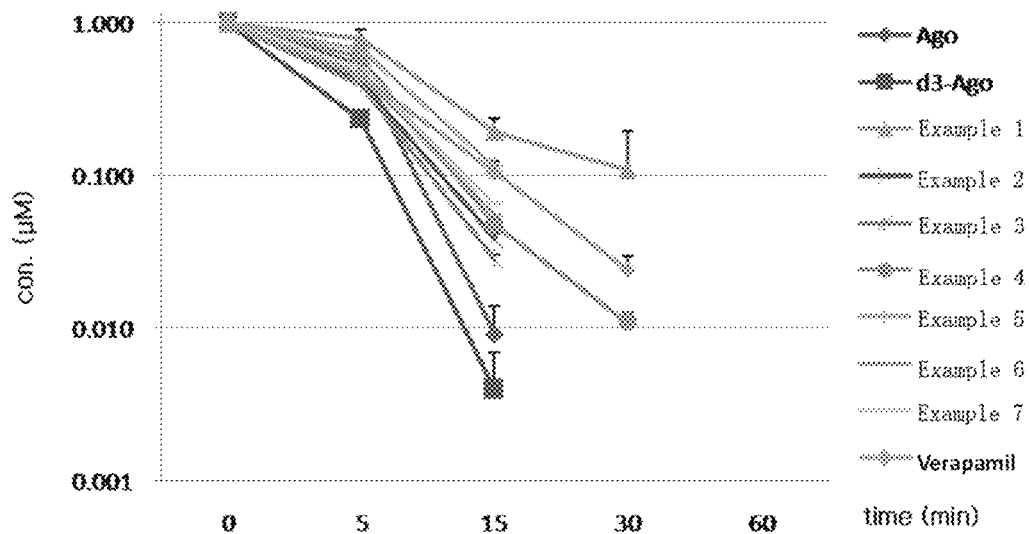
FIG. 2 shows the results of the metabolic stability test in vitro for the compounds of Examples 1, 2, 3, 4, 5, 6 and 7 and the controls Ago and d3-Ago.

Approximately 10 mg of each sample to be tested was accurately weighed, dissolved in 0.1 mL of DMSO, and serially diluted with purified water to a 10 μM, 1 μM standard stock solution. An ice bath was operated and the incubation system for detection was formulated according to Table 4. NADPH was added to the incubation system to start the reaction, and then 50 μL was immediately added to 150 μL acetonitrile as a zero-time sample and a 1 μM standard curve sample. Another 1 μM standard stock solution was added to the incubation system, and then 50 μL was immediately added to 150 μL acetonitrile as a 0.1 μM standard curve sample. The remaining systems were kept in a water bath at 37° C., and 50 μL was added to 150 μL acetonitrile at 5 min, 15 min, 30 min, 1 h, and 2 h, respectively. Each sample was shaken, and centrifuged at 18000 g for 10 min. The supernatant was taken for LC/MS/MS injection and determination. The results of test data of some of example compounds were shown in Table 5 below, and the results of visualization were shown in FIG. 2.

TABLE 4

Composition of the incubation system

| Stock solution | Original concentration | Added volume (μl) | Final concentration |
|---|---|---|---|
| PBS | 0.1M | 195 | |
| MgCl$_2$ | 20 mM | 30 | 2 mM |
| Microsome | 20 mg/mL | 15 | 1 mg/mL |
| Sample to be tested | 10 μM | 30 | 1 μM |
| NADPH | 10 mM | 30 | 1 mM |
| total volume | | 300(μL) | |

TABLE 5

Concentrations (μM) measured at each time point of compounds to be tested

| | Incubation time (min) | | | | |
|---|---|---|---|---|---|
| | 0 | 5 | 15 | 30 | 60 |
| Ago | 0.999 ± 0.059 | 0.539 ± 0.019 | 0.009 ± 0.005 | | |
| d3-Ago | 0.999 ± 0.103 | 0.235 ± 0.022 | 0.004 ± 0.003 | | |
| Example 1 | 1.001 ± 0.019 | 0.793 ± 0.108 | 0.194 ± 0.046 | 0.110 ± 0.088 | |
| Example 2 | 1.000 ± 0.036 | 0.420 ± 0.079 | 0.039 ± 0.003 | | |
| Example 3 | 1.000 ± 0.041 | 0.395 ± 0.047 | 0.029 ± 0.002 | | |
| Example 4 | 1.001 ± 0.017 | 0.601 ± 0.009 | 0.048 ± 0.003 | 0.011 ± 0.002 | |
| Example 5 | 1.000 ± 0.032 | 0.675 ± 0.044 | 0.116 ± 0.010 | | |
| Example 6 | 1.000 ± 0.042 | 0.471 ± 0.051 | 0.056 ± 0.005 | | |
| Example 7 | 1.000 ± 0.035 | 0.505 ± 0.033 | 0.065 ± 0.007 | | |
| Verapamil | 1.000 ± 0.054 | 0.455 ± 0.042 | 0.106 ± 0.011 | 0.024 ± 0.006 | |

Verapamil's metabolism proved that the detection system was normal. The results of the control and the examples showed that the compounds were metabolized fast in human liver microsome, and were lower than the minimum detection limit after 60 minutes; the metabolic stabilities of the example compounds were better than those of the control compounds Agomelatine and d3-Agomelatine; the compound of Example 1 had the highest metabolic stability.

2. In Vivo Metabolism Study

In a test of a rat oral/tail vein injection model using Agomelatine as a control, pharmacokinetic parameters such as the plasma concentration exposure of the compound of Example 1 were compared with those of the control drug to evaluate the metabolic stability in vivo.

Formulation of a solution for intravenous administration: approximately 5 mg of each test drug was accurately weighed, and dissolved in 50 μL of DMSO. To the solution was added an appropriate amount of 40% PEG400 aqueous solution to prepare a 0.5 mg/mL solution. The administration volume was 0.2 mL/200 g body weight, and the dose was 0.5 mg/kg body weight according to concentration conversion.

Formulation of a solution for i.g. administration: approximately 5 mg of each test drug was accurately weighed, and suspended and dispersed with a 1% aqueous solution of HPMC to prepare a 1 mg/mL suspension. The administration volume was 1 mL/200 g body weight, and the dose was 5 mg/kg body weight in terms of concentration according to concentration conversion.

Rats were randomly divided into 4 groups of 5 rats each. Oral gavage and tail vein administration were carried out according to the above dosages. At 2 min, 5 min, 15 min, 30 min, 1 h, 1.5 h, 2 h, and 3 h after administration, blood was collected from an orbit, and centrifuged at 8000 rpm for 10 min. 50 μL of plasma was weighed, and added with 50 μL of internal standard and 150 μL of acetonitrile. The mixture was mixed by shaking, and centrifuged at 18000 rpm for 10 min. The supernatant was taken for LC/MS/MS injection and determination. The determined data were analyzed using a DAS pharmacokinetic program to calculate the main pharmacokinetic parameters. The test results were shown in Table 6 below.

TABLE 6

Pharmacokinetic parameters of rats after oral or tail vein injection administration.

| | Example 1 | | Agomelatine | |
|---|---|---|---|---|
| | Oral 5 mg/kg | Intravenous injection 0.5 mg/kg | Oral 5 mg/kg | Intravenous injection 0.5 mg/kg |
| AUC(0-t) (μg/L*h) | 248.83 | 48.93 | 51.57 | 102.12 |
| t$_{1/2}$ (h) | 0.49 | 0.48 | 0.67 | 0.34 |
| F % | 50.90% | | 5.05% | |

The results showed that the plasma exposure AUC (0-t) of the rats with oral administration of Example 1 was significantly increased (248.8 Vs 51.6) compared with that of the rats with the oral administration of Agomelatine. According to a dose conversion, the bioavailability was significantly increased (50.90% Vs 5.05%).

Part IV: Animal Behavior Study of Example Compounds

1. Behavior Despair Model

Animals: Kunming mice, male, body weight 18-22 g, SPF grade; SD rats, male, body weight 150-180 g, SPF grade. The test was carried out after acclimatization, and the animal was fasted for 12 hours before the test.

All drugs for the test were suspended and dispersed in a 1% aqueous solution of hydroxypropyl methylcellulose (HPMC), and shaken well before use. A blank control group (control), a positive drug group (Agomelatine) and a test group (Examples 1, 2, 3, 4, and 5) were established. The doses for administration were all 10 mg/kg. For the concentration and volume for administration, see J Psychiatry Neurosci 2004; 29(2):126-133. The mice were intraperitoneally administered in a volume of 0.5 mL/20 g; and the rats were administered by i.g. in a volume of 2 mL/100 g.

1.1 the Tail Suspension Test (TST) in Mice

Mice were randomly divided into groups according to weight balance. Intraperitoneal injection was administered for three consecutive days, once a day, and the tail suspension test were performed 30 minutes after the third day. The tail suspension box was 25×25×35 cm, and a small clip was connected with a rope at the center of the top plate. An adhesive tape was stuck to the tail of the mouse 2 cm away from the tail end, and the adhesive tape was clamped with the clip to make the mouse in an inverted position. The duration of immobility was recorded during the last 4 minutes of total 6 minutes observed. The results were shown in Table 7.

TABLE 7

Results of tail suspension test (TST) in mice of compounds (10 mg/kg)

| Group | Immobility time (s) |
| --- | --- |
| Control | 111.6 ± 20.3 |
| Agomelatine | 75.1 ± 21.4 |
| Example 1 | 55.7 ± 19.7** |
| Example 2 | 69.4 ± 23.3* |
| Example 3 | 77.7 ± 28.6 |
| Example 4 | 76.6 ± 18.4 |
| Example 5 | 68.8 ± 17.3* |

Note:
n = 10,
*$P < 0.05$
**$P < 0.01$
***$P < 0.001$ compared with the control group 1.2 Forced Mouse Swimming Test Animal grouping and administration method were the same as those in the tail suspension test in mice. The mice were placed in a round glass vessel with a height of 20 cm, an inner diameter of 12 cm, a water depth of 10 cm and a water temperature of 25° C. The mice were observed for 6 minutes and the accumulated immobility time in the last 4 minutes was recorded. The results were shown in Table 8.

TABLE 8

Results of forced mouse swimming test of compounds (10 mg/kg)

| Group | Immobility time (s) |
| --- | --- |
| Control | 148.4 ± 29.1 |
| Agomelatine | 113.5 ± 26.6 |
| Example 1 | 73.0 ± 18.2*** |
| Example 2 | 81.3 ± 20.3*** |
| Example 3 | 83.3 ± 30.7*** |
| Example 4 | 75.6 ± 26.7*** |
| Example 5 | 96.4 ± 14.4* |

Note:
n = 10,
*$P < 0.05$
**$P < 0.01$
***$P < 0.001$ compared with the control group 1.3 Forced Rat Swimming Test Rats were randomly divided into groups according to weight balance. Rats were administered by i.g. for three consecutive days, once a day. One hour after administration on the third day, the forced swimming test was performed. The rats were placed in a round glass jar with a height of 40 cm, an inner diameter of 18 cm, a water depth of 23 cm, and a water temperature of 25° C. The rats were allowed to swim for 6 minutes, and the accumulated immobility time in the last 5 minutes was recorded. The results were shown in Table 9.

TABLE 9

Results of forced rat swimming test of compounds (10 mg/kg)

| Group | Immobility time (s) |
| --- | --- |
| Control | 123.7 ± 40.3 |
| Agomelatine | 73.5 ± 38.5* |
| Example 1 | 51.0 ± 32.4*** |
| Example 2 | 61.3 ± 29.8** |
| Example 3 | 76.1 ± 30.2* |
| Example 4 | 71.4 ± 40.3* |
| Example 5 | 66.2 ± 35.1* |

Note:
n = 8,
*$P < 0.05$
**$P < 0.01$
***$P < 0.001$ compared with the control group Among the behavior despair models, Example 1 had the best antidepressant efficacy.

2. Chronic Unpredictable Stress Model of Rat

Animals: SD rats, male, weighing 150-180 g, SPF grade.

Formulation and administration mode of drugs: All drugs for the test were suspended and dispersed with a 0.5% aqueous solution of CMC-Na, and shaken well before use. The rats were administered by i.g. at a volume of 10 mL/kg.

A normal control group (no stress, control), a stress model group (stress), a positive drug group (stress+Agomelatine, 10/20/40 mg/kg), and a test group (stress+Example 1, 5/10/20/40 mg/kg) were established.

Figure 3:
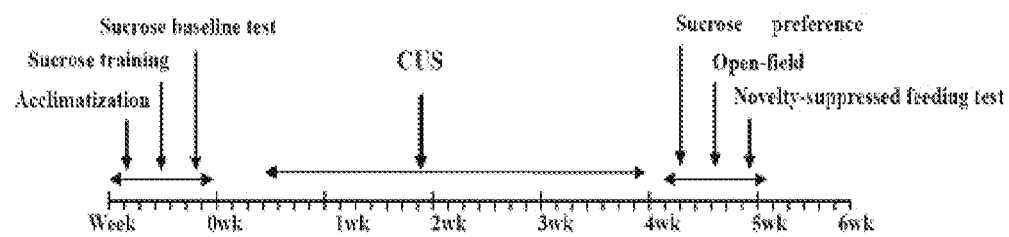
FIG. 3 shows a chronic stress process for a rat.

The test flow was shown in FIG. 3. Rats were acclimatized for 3 days after purchase. First, 48 h of sucrose training was performed. After the training, a sucrose baseline test was performed. The rats were randomly and evenly grouped according to sucrose preference. Then, (dl) a 4-week chronic unpredictable stress (CUS) procedure was performed with the following stress methods: (1) food deprivation (fasting); (2) water deprivation; (3) stroboflash; (4) overnight illumination; (5) wet feeding (200 ml of water was added to 150 g of sawdust bedding); (6) noise stimulation (110 dB), 1 h;

(7) swimming in cold water (the water temperature was 10° C.); (8) cage tilt (45 degrees of inclination); (9) tail pinch (at 1 cm away from the tail root) for 6 min; (10) restraint for 1-2 h. One of the above stress methods was used randomly every day, but water deprivation and fasting were separated. The corresponding drugs (including the blank control group and the positive drug group) were given 1 h before the stress in the morning every day. Behavior test was performed after the end of the chronic stress. d25, sucrose preference; d28, open-field; d31, novelty-suppressed feeding test.

2.1 Sucrose Preference Test

Rats were acclimatized for 3 days after purchase. The rats were trained to give sucrose aqueous solution for 48 h without food and water supply, only 1% aqueous solution of sucrose was given for the first 24 h, and 1% aqueous solution of sucrose and tap water were simultaneously given for the next 24 h. After the end of the training, the rats were fed with normal food and water for 3 days, and then a sucrose preference baseline was determined: after fasting and water deprivation for 14 h, rats were allowed to drink freely two different bottles of water, one of which was 1% aqueous solution of sucrose and the other was tap water. The intakes (g) of rats from these two bottles within 1 hour were measured to calculate the sucrose preference. Sucrose preference (%)=intake of aqueous solution of sucrose/(intake of aqueous solution of sucrose+intake of tap water)×100%. On the $25^{th}$ day of the stress program, the same method was used to perform the sucrose preference test again to calculate the sucrose preference.

TABLE 10

Effect of example compound 1 on sucrose preference of chronic stress rat

| Group | Drug dose (mg/kg) | Sucrose preference (%) | |
|---|---|---|---|
| | | Before modeling | After 4 weeks of administration |
| Control | — | 62.3 ± 2.8 | 71.6 ± 5.3 |
| Stress | — | 58.8 ± 7.1 | 50.2 ± 6.1# |
| Stress + Agomelatine | 10 | 65.5 ± 4.2 | 84.3 ± 3.6*** |
| | 20 | 65.6 ± 10.1 | 66.6 ± 6.7 |
| | 40 | 60.5 ± 6.1 | 76.1 ± 5.3** |
| Stress + Example 1 | 5 | 55.5 ± 7.8 | 80.4 ± 3.1*** |
| | 10 | 58.8 ± 5.1 | 78.4 ± 4.4** |
| | 20 | 60.1 ± 4.4 | 78.8 ± 6.1*** |
| | 40 | 70.3 ± 4.1 | 83.3 ± 1.9*** |

Note:
n = 9-12,
***P < 0.001,
**P < 0.01 compared with the model group,
P < 0.05 compared with the control group.

2.2 Open-Field Activity Test of Rat

On the $28^{th}$ day of the stress program, the rats were placed in the middle compartment of an open chamber, and a 60 W light bulb was placed 45 cm directly above them. The activities of the rats were observed within 5 minutes, including the number of times crossing a compartment horizontally (the number of times crossing into an adjacent compartment with three or more claws), and the number of times rearing (the number of times the forelimbs are more than 1 cm off the ground). Note: the test environment of the test should be kept as quiet as possible; the rats should be placed in the same position and direction each time; and the animal's excretion should be removed after each test.

TABLE 11

Effect of example compound 1 on the open-field activity of chronic stress rat

| | | Activity | |
|---|---|---|---|
| Group | Drug dose (mg/kg) | Number of times crossing a compartment horizontally | Number of times rearing |
| Control | — | 41.2 ± 2.9 | 18.8 ± 1.4 |
| Stress | — | 11.7 ± 1.8### | 7.9 ± 1.2### |
| Stress + Agomelatine | 10 | 33.4 ± 4.2** | 18.1 ± 1.1*** |
| | 20 | 33.9 ± 2.4** | 16.7 ± 1.8*** |
| | 40 | 38.9 ± 3.6*** | 17.3 ± 1.1*** |
| Stress + Example 1 | 5 | 36.8 ± 4.4** | 15.1 ± 1.3** |
| | 10 | 36.4 ± 4.2** | 14.6 ± 1.7** |
| | 20 | 36.5 ± 2.9*** | 15.9 ± 1.1*** |
| | 40 | 34.9 ± 3.0** | 17 ± 1.5*** |

Note:
n = 9-12,
**P < 0.01,
***P < 0.001, compared with the model group,
P < 0.001, compared with the control group.

2.3 Novelty-Suppressed Feeding Test of Rat

On the $29^{th}$ day of the stress program, the rats were fasted for 48 hours (not water deprivation) and then subjected to a novelty-suppressed feeding test (d31). The rats were placed in a novelty-suppressed feeding chamber with an open top. The bottom of the chamber was covered with a 2 cm thick sawdust. In the center of the chamber were placed 12 food balls of the same size. At the same time as the rats were put in, the latency of the rats to start eating within 5 min was calculated. The criterion for eating was that the animal started chewing food instead of just sniffing or toying with food. Rats that had not eaten within 5 minutes were recorded to have a feeding latency of 5 minutes. The test environment of the test should be kept as quiet as possible; the rats should be placed in the same position and direction each time; the environment of the test was preferably different from the breeding environment, and the light intensity of the test environment was greater than that of the breeding environment.

TABLE 12

Effect of example compound 1 on novelty-suppressed feeding latency of chronic stress rat

| Group | Drug dosage (mg/kg) | Feeding latency (s) |
|---|---|---|
| Control | — | 171 ± 32 |
| Stress | — | 274 ± 10** |
| Stress + Agomelatine | 10 | 248 ± 21 |
| | 20 | 164 ± 26## |
| | 40 | 130 ± 17### |
| Stress + Example 1 | 5 | 188 ± 21# |
| | 10 | 145 ± 23### |
| | 20 | 115 ± 16### |
| | 40 | 117 ± 14### |

Note:
n = 9-12,
**P < 0.01, compared with the control group,
P < 0.05,
P < 0.01,
P < 0.001, compared with the model group.

In the chronic mild stress model, Example 1 can increase the sucrose preference of the stress rat, increase the number of cross-compartment times and rearing times, and shorten the feeding latency, proving that it has an anti-depressant effect and its anti-depressant effect is stronger than that of Agomelatine.

3. Anxiety Behavior Model of Repeatedly Administrated Rat

The requirements for test animals, drug formulation and administration were the same as those of the rat chronic mild stress model.

Instruments: Vogel drinking anxiety device for rat and O-maze device for rat were manufactured by Shanghai XinRuan Company. The rat feeding chamber was a homemade white plastic box (60×45×25 cm).

Rats were randomly grouped, and a blank control group (control), a positive drug group (Agomelatine 10/20/40 mg/kg), and a test group (Example 1, 5/10/20/40 mg/kg) were established. The rats were administrated continuously by i.g. once a day. A novelty-suppressed feeding test, a Vogel drinking conflict test, and an O-maze test were performed on a different day, respectively. Each behavior test was performed at 9:00-12:00, and the administration time was 16:00-17:00. The test process was as follows: D12, novelty-suppressed feeding test (animals were fasted for 48 hours before the test); D18, Vogel drinking conflict test (animals were banned from water for 48 hours before the test); D21, O-maze test.

3.1 Novelty-Suppressed Feeding Test of Rat

Common paddings with a thickness of 1.5 cm were placed at the floor of the rat feeding chamber, and six equal-sized food pellets were placed in the center. During the test, the rats were individually placed in a fixed position of the feeding chamber, and observed for 5 minutes. The time from rat entry to the start of biting or chewing the food was recorded with a stopwatch.

TABLE 13

Effect of chronic administration of example compound 1 on novelty-suppressed feeding latency of rat

| Group | Drug dosage (mg/kg) | Feeding latency (s) |
| --- | --- | --- |
| Control | — | 224 ± 22 |
| Agomelatine | 10 | 208 ± 26 |
|  | 20 | 163 ± 25 |
|  | 40 | 124 ± 25** |
| Example 1 | 5 | 232 ± 23 |
|  | 10 | 141 ± 17* |
|  | 20 | 124 ± 18** |
|  | 40 | 120 ± 14** |

Note:
n = 9-12,
*$P < 0.05$,
**$P < 0.01$,
***$P < 0.001$ compared with the control group.

3.2 Vogel Drinking Conflict Test of Rat

The Vogel drinking anxiety device for rat connected a drinking tube of a water bottle, an electric grid and a current loop of a controller through the animal body when rat drank water. The controller can automatically record the number of times the animal drank water and can deliver an electric shock to foot sole. The rat was individually placed in the test chamber after 48 hours of water deprivation. When the animal drank 20 times in the test chamber, the controller started timing for 3 minutes, and every 20 times the rat drank, one electric shock to foot sole was delivered (0.35 mA for 2 s). The device automatically recorded the number of times the rat drank water with electric shock within 3 minutes.

TABLE 14

Effect of chronic administration of example compound 1 on Vogel shock conflict drinking behavior of rat

| Group | Drug dosage (mg/kg) | Number of times drinking water with electric shock (s) |
| --- | --- | --- |
| Control | — | 71 ± 9 |
| Agomelatine | 10 | 121 ± 28 |
|  | 20 | 123 ± 25 |
|  | 40 | 180 ± 28** |
| Example 1 | 5 | 76 ± 11 |
|  | 10 | 159 ± 14* |
|  | 20 | 172 ± 25* |
|  | 40 | 213 ± 20*** |

Note:
n = 9-12,
*$P < 0.05$,
**$P < 0.01$,
***$P < 0.001$ compared with the control group.

3.3 O-Maze Test of Rat

An O-maze device was placed in the center of a dark room and illuminated with an infrared light during the test. The animal was placed in the center of a closed arm of an O-maze track, timed for 5 minutes, and the activity of the rat in the maze was monitored by an infrared camera. Animals in each group were given a single intragastric administration 60 min before the test. Observation indicators were the number of times the rat entered the open arm and the accumulated dwell time in the open arm.

TABLE 15

Effect of long-term administration of example compound 1 on rat O-maze behavior

| Group | Drug dose (mg/kg) | Activity | |
| --- | --- | --- | --- |
|  |  | Number of times entering the open arm | Dwell time in the open arm (s) |
| Control | — | 1 ± 0.3 | 101 ± 15 |
| Agomelatine | 10 | 2.25 ± 0.4 | 126 ± 15 |
|  | 20 | 3.1 ± 0.8 | 196 ± 30* |
|  | 40 | 6.2 ± 1.0*** | 170 ± 29 |
| Example 1 | 5 | 4.8 ± 0.9* | 131 ± 30 |
|  | 10 | 8.8 ± 0.9*** | 201 ± 17* |
|  | 20 | 10.89 ± 0.7*** | 245 ± 6*** |
|  | 40 | 6.3 ± 1.1*** | 171 ± 27 |

Note:
n = 9-12,
*$P < 0.05$,
**$P < 0.01$,
***$P < 0.001$, compared with the control group.

In the anxiety behavior model of repeatedly administrated rats, Example 1 can reduce the feeding latency of rats in the anxiety model, increase the frequency of drinking water with electric shock, and increase the exploration behavior of the O-maze open arm, proving that it has an anti-anxiety effect stronger than that of Agomelatine.

Part V: Preliminary Safety Evaluation of Example Compounds

The requirements for test animals were the same as those in the fourth part "behavior study/behavior despair model." With Agomelatine as a control drug, the safety of a single administration was preliminarily judged.

1. Acute Toxicity Test of Mouse

Mice were randomly grouped according to body weight with each group of 10 mice, and an Example 1 group, an Agomelatine control group and a blank control group were established. Mice were administered by i.g. at doses of 5000 mg/kg and 2000 mg/kg. The drugs were dispersed with a 1% aqueous solution of hydroxypropyl methylcellulose (HPMC), and the administration volume was calculated in accordance with 0.2 mL/10 g. The mice were observed for 14 days after the administration and then sacrificed.

Example 1, 5000 mg/kg group: the mice began to fall into a coma 15 minutes after the administration, and within 24 hours the mice all awakened and returned to normal. The mice had no obvious adverse reactions within 14 days after the administration, and their diet and behavior were normal. There was no significant difference in body weight compared with the blank group.

Example 1, 2000 mg/kg group: after the administration, the activity of the mice became slightly smaller but there were no obvious adverse reactions. The mice had no obvious adverse reactions within 14 days after the administration, and their diet and behavior were normal. There was no significant difference in body weight compared with the blank group.

Agomelatine, 5000 mg/kg group: the mice all fell into a coma 15 minutes after the administration and died successively after 12 hours.

Agomelatine, 2000 mg/kg group: the mice all fell into a coma 15 minutes after the administration, 4 mice died within 12 hours, and all other mice awakened and returned to normal within 24 hours. The mice had no obvious adverse reactions within 14 days after the administration, and their diet and behavior were normal. Compared with the blank group, the body weight was lighter on the first and second days after the administration with a significant difference, and returned to normal at the seventh and fourteenth days.

Results: In the mouse model, Example 1 was safer than the control drug Agomelatine.

2. Acute Toxicity Test of Rat

Rats were randomly grouped according to body weight with each group of 10 rats, and an Example 1 group, an Agomelatine control group and a blank control group were established. Rats were administered by i.g. at a dose of 2000 mg/kg. The drugs were dispersed with a 1% aqueous solution of hydroxypropyl methylcellulose (HPMC). The rats were observed for 14 days after administration and then sacrificed.

Example 1, 2000 mg/kg group: after the administration, the activity of the rats became slightly smaller but there were no obvious adverse reactions. The rats had no obvious adverse reactions within 14 days after the administration, and their diet and behavior were normal. There was no significant difference in body weight compared with the blank group.

Agomelatine, 2000 mg/kg group: 15 minutes after the administration, 8 rats were slow to move or became lethargic, and all returned to normal within 2 hours. The rats had no obvious adverse reactions within 14 days after the administration, and their diet and behavior were normal. There was no significant difference in body weight compared with the blank group.

Results: In the rat model, example 1 was safer than the control drug Agomelatine.

Part VI: Pharmaceutical Compositions Comprising the Example Compounds 1000 tablets were prepared, each containing 10 mg dose, with the formulae as follows:

| Formula 1 | | Formula 2 | |
|---|---|---|---|
| Example 1 compound | 10 g | Example 1 compound | 10 g |
| Lactose monohydrate | 62 g | Lactose monohydrate | 62 g |
| Magnesium stearate | 1.3 g | Magnesium stearate | 1.3 g |
| Stearic acid | 2.6 g | Stearic acid | 2.6 g |
| corn starch | 26 g | Povidone | 9 g |
| Maltodextrin | 9 g | Anhydrous colloidal silica | 0.3 g |
| Anhydrous colloidal silica | 0.3 g | Sodium hydroxymethyl cellulose | 30 g |
| Type A sodium strach glycollate | 4 g | | |

It should be noted that the technical features in the embodiments of the present application can be used in any combination in the absence of conflict.

Although the specific embodiments of the present invention have been described in detail, those skilled in the art will understand that according to all the teachings disclosed, various modifications and substitutions can be made to those details, and these changes are all within the protection scope of the present invention. The protection scope of the invention is given by the appended claims and any equivalents thereof.

What is claimed is:

1. A compound of formula I, or a pharmaceutically acceptable salt thereof, or a mixture thereof,

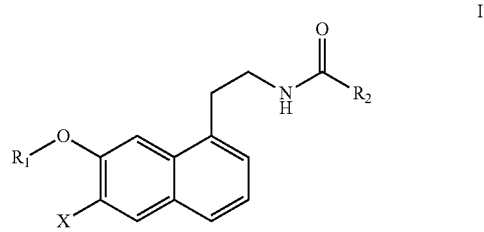

wherein:
X is fluorine or chlorine;
$R_1$ is $CH_3$ or $CD_3$;
$R_2$ is $CH_3$ or $C_2H_5$;
with the proviso that the compound of formula I excludes N-(2-(6-fluoro-7-methoxy-naphthalen-1-yl)ethyl) acetamide.

2. The compound of formula I, or the pharmaceutically acceptable salt thereof, or the mixture thereof according to claim 1, wherein $R_1$ is $CD_3$.

3. The compound of formula I, or the pharmaceutically acceptable salt thereof, or the mixture thereof according to claim 1, which is selected from the group consisting of:
N-(2-(6-chloro-7-deuteromethoxy-naphthalen-1-yl)ethyl) acetamide;
N-(2-(6-chloro-7-methoxy-naphthalen-1-yl)ethyl)acetamide;
N-(2-(6-fluoro-7-deuteromethoxy-naphthalen-1-yl)ethyl) acetamide;
N-(2-(6-chloro-7-deuteromethoxy-naphthalen-1-yl)ethyl) propanamide;
N-(2-(6-chloro-7-methoxy-naphthalen-1-yl)ethyl)propanamide; and
N-(2-(6-fluoro-7-methoxy-naphthalen-1-yl)ethyl)propanamide.

4. The compound of formula I, or the pharmaceutically acceptable salt thereof, or the mixture thereof according to claim 1, which is selected from the group consisting of:

N-(2-(6-chloro-7-deuteromethoxy-naphthalen-1-yl)ethyl)acetamide hydrochloride;

N-(2-(6-chloro-7-methoxy-naphthalen-1-yl)ethyl)acetamide hydrochloride;

N-(2-(6-chloro-7-methoxy-naphthalen-1-yl)ethyl)acetamide sulfate; and

N-(2-(6-chloro-7-methoxy-naphthalen-1-yl)ethyl)acetamide methanesulfonate.

5. The compound of formula I, or the pharmaceutically acceptable salt thereof, or the mixture thereof according to claim 1, which is N-(2-(6-chloro-7-deuteromethoxy-naphthalen-1-yl)ethyl)acetamide, or a pharmaceutically acceptable salt thereof, or a mixture thereof.

6. The compound of formula I, or the pharmaceutically acceptable salt thereof, or the mixture thereof according to claim 1, which is N-(2-(6-chloro-7-methoxy-naphthalen-1-yl)ethyl)acetamide, or a pharmaceutically acceptable salt thereof, or a mixture thereof.

7. The compound of formula I, or the pharmaceutically acceptable salt thereof, or the mixture thereof according to claim 1, which is N-(2-(6-fluoro-7-deuteromethoxy-naphthalen-1-yl)ethyl)acetamide, or a pharmaceutically acceptable salt thereof, or a mixture thereof.

8. The compound of formula I, or the pharmaceutically acceptable salt thereof, or the mixture thereof according to claim 1, which is N-(2-(6-chloro-7-deuteromethoxy-naphthalen-1-yl)ethyl)propanamide, or a pharmaceutically acceptable salt thereof, or a mixture thereof.

9. The compound of formula I, or the pharmaceutically acceptable salt thereof, or the mixture thereof according to claim 1, which is N-(2-(6-chloro-7-methoxy-naphthalen-1-yl)ethyl)propanamide, or a pharmaceutically acceptable salt thereof, or a mixture thereof.

10. The compound of formula I, or the pharmaceutically acceptable salt thereof, or the mixture thereof according to claim 1, which is N-(2-(6-fluoro-7-methoxy-naphthalen-1-yl)ethyl)propanamide, or a pharmaceutically acceptable salt thereof, or a mixture thereof.

11. A pharmaceutical composition, comprising:
a therapeutically and/or prophylactically effective amount of the compound of formula I, or the pharmaceutically acceptable salt thereof, or the mixture thereof according to claim 1; and
a pharmaceutically acceptable adjuvant.

12. A pharmaceutical combination, comprising:
a) one or more first active ingredient(s) selected from the compound of formula I, or the pharmaceutically acceptable salt thereof, or the mixture thereof according to claim 1, and
b) one or more additional active ingredient(s) selected from the group consisting of a melatonin receptor agonist and a 5-HT$_{2C}$ receptor antagonist.

13. A method for synthesizing the compound of formula I of claim 1, comprising:
carrying out a Friedel-Crafts reaction between methoxybenzene ortho-substituted with halogen and succinic anhydride in the presence of a catalyst to give an aromatic ketone intermediate

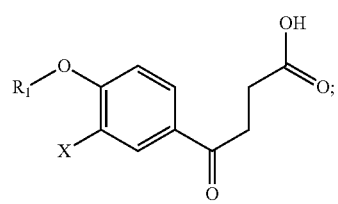

reducing a carbonyl group of the aromatic ketone intermediate to a methylene group with triethylsilane to give an aromatic butanoic acid intermediate

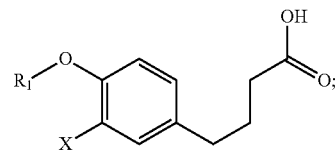

cyclizing the aromatic butanoic acid intermediate under an action of an acidic catalyst to give a tetralin intermediate

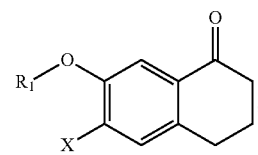

cyanating the tetralin intermediate with cyanoacetic acid to give a dihydronaphthylacetonitrile intermediate

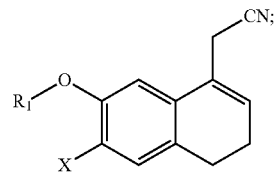

dehydrogenating the dihydronaphthylacetonitrile intermediate to give a naphthylacetonitrile intermediate

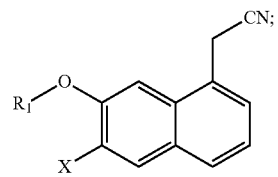

and reacting the naphthylacetonitrile intermediate with sodium borohydride and acetic anhydride or propionic anhydride in the presence of a catalyst nickel chloride hexahydrate to give a compound of formula I.

14. The method according to claim 13, further comprising:
dissolving the compound of formula I in toluene to react with anhydrous aluminum trichloride to give a naphthol compound; and
reacting the naphthol compound with deuterated methyl iodide to give a deuterated compound of formula I.

15. The method according to claim 13, further comprising:
reacting the compound of formula I with an acid to form a salt.

16. The method according to claim 14, further comprising:

reacting the compound of formula I with an acid to form a salt.

* * * * *